US012746299B2

(12) United States Patent
Radford et al.

(10) Patent No.: US 12,746,299 B2
(45) Date of Patent: Sep. 29, 2026

(54) ANTIMICROBIAL COMPOUNDS BASED ON GLUCOHEPTONIC ACIDS AND THEIR SALTS

(71) Applicant: HARCROS CHEMICALS, INC., Kansas City, MO (US)

(72) Inventors: Peter Radford, Lenexa, KS (US); Diana Crain, Overland Park, KS (US); Larry Morris, Smithville, MO (US); Kevin Sikkema, Overland Park, KS (US); Amol Ashok Walke, Mapusa Bardez Goa (IN); Jose C. J. M. D. S. Menezes, Bicholim-Goa (IN); Prasanta Mayapur, Mapusa Bardez (IN)

(73) Assignee: HARCROS CHEMICALS, INC., Kansas City, MO (US)

( * ) Notice: Subject to any disclaimer, the term of this patent is extended or adjusted under 35 U.S.C. 154(b) by 583 days.

(21) Appl. No.: 18/270,508

(22) PCT Filed: Feb. 3, 2022

(86) PCT No.: PCT/IB2022/050962
§ 371 (c)(1),
(2) Date: Jun. 30, 2023

(87) PCT Pub. No.: WO2022/144867
PCT Pub. Date: Jul. 7, 2022

(65) Prior Publication Data

US 2024/0197938 A1 Jun. 20, 2024

Related U.S. Application Data

(60) Provisional application No. 63/133,440, filed on Jan. 4, 2021.

(51) Int. Cl.
*A61L 2/18* (2026.01)
*A01N 37/36* (2006.01)
*A01N 47/44* (2006.01)

(52) U.S. Cl.
CPC ................ *A61L 2/18* (2013.01); *A01N 37/36* (2013.01); *A01N 47/44* (2013.01)

(58) Field of Classification Search
CPC ..... A61L 2/18; A61K 2800/524; A61K 8/365; A61K 8/416; A61K 8/43; A01P 1/00;
(Continued)

(56) References Cited

U.S. PATENT DOCUMENTS 2,725,326 A 11/1955 Shibe, Jr. et al.
2,735,866 A 2/1956 Clevenot
(Continued)

FOREIGN PATENT DOCUMENTS

DE 34 43 232 A1 6/1985
EP 0 726 885 B1 3/1999
(Continued)

OTHER PUBLICATIONS

Jang, S.H. et al., "A Systematic Method for Reducing Surfactant Retention to Extremely Low Levels", Society of Petroleum Engineers, Apr. 11, 2016, doi:10.2118/179685-MS (34 pgs).
(Continued)

*Primary Examiner* — Jennifer Wecker
*Assistant Examiner* — Brady C Pilsbury
(74) *Attorney, Agent, or Firm* — Stinson LLP

(57) ABSTRACT

The invention relates to methods for disinfecting or sanitizing. The invention is also directed to methods for the preparation of certain compounds useful as a disinfectant or sanitizer, such as glucoheptonic acid, chlorhexidine digluconate, benzalkonium glucoheptonate, and combinations thereof. The invention is still further directed to
(Continued)

methods for evaluating a compound for performance in microbial disinfecting or sanitizing.

20 Claims, 14 Drawing Sheets

(58) Field of Classification Search
CPC .. A01P 3/00; C11D 3/48; C11D 7/265; A01N 47/44
See application file for complete search history.

(56) References Cited

U.S. PATENT DOCUMENTS

| | | | | |
|---|---|---|---|---|
| 3,539,464 | A * | 11/1970 | Harper | C07C 59/105 510/531 |
| 3,679,659 | A | 7/1972 | Zak | |
| 3,691,013 | A | 9/1972 | Sakai et al. | |
| 4,919,837 | A | 4/1990 | Gluck | |
| 5,435,845 | A * | 7/1995 | Villa | C04B 24/06 106/729 |
| 5,719,113 | A | 2/1998 | Fendler et al. | |
| 5,965,514 | A | 10/1999 | Wierenga et al. | |
| 6,312,577 | B1 | 11/2001 | Ganzi et al. | |
| 6,500,466 | B2 | 12/2002 | Werle et al. | |
| 6,531,434 | B1 | 3/2003 | Gluck | |
| 8,961,813 | B2 | 2/2015 | Kiely et al. | |
| 9,511,017 | B2 | 12/2016 | Kritzler | |
| 9,642,846 | B2 | 5/2017 | Calderone et al. | |
| 10,813,357 | B1 | 10/2020 | Macinga et al. | |
| 2002/0018814 | A1 | 2/2002 | Werle et al. | |
| 2002/0072480 | A1 | 6/2002 | Werle et al. | |
| 2002/0155969 | A1 | 10/2002 | Rees et al. | |
| 2006/0062753 | A1 | 3/2006 | Naraghi et al. | |
| 2007/0282044 | A1* | 12/2007 | Cavanaugh | C08L 27/18 524/502 |
| 2010/0277207 | A1 | 11/2010 | Kemp et al. | |
| 2011/0117032 | A1 | 5/2011 | Gilding | |
| 2012/0289742 | A1* | 11/2012 | Gerberding | C12P 7/46 562/580 |
| 2015/0005225 | A1 | 1/2015 | Tulchinsky et al. | |
| 2016/0318837 | A1 | 11/2016 | Kon et al. | |
| 2017/0265476 | A1 | 9/2017 | Reubens | |

FOREIGN PATENT DOCUMENTS

| | | | |
|---|---|---|---|
| EP | 1 732 878 B1 | 6/2014 | |
| WO | 1998/005206 | 2/1998 | |
| WO | WO-2018033718 A1 * | 2/2018 | A61K 8/416 |
| WO | 2020/055716 A1 | 3/2020 | |

OTHER PUBLICATIONS

Fortenberry, R. et al., "Use of Cosolvents to Improve Alkaline/Polymer Flooding", Society of Petroleum Engineers, Apr. 1, 2015, doi:10.2118/166478-PA (13 pgs).

Adkins, S. et al., "Development of Thermally and Chemically Stable Large-Hydrophobe Alkoxy Carboxylate Surfactants", Society of Petroleum Engineers, Apr. 2012, doi:10.2118/154256-MS (11 pgs).

Lu, J. et al., "Recent Technology Developments in Chemical Enhanced Oil Recovery", International Petroleum Technology Conference, Mar. 26-28, 2013, doi:10.2523/IPTC-16425-MS (15 pgs).

Upamali, A. et al., "New Surfactants and Co-Solvents Increase Oil Recovery and Reduce Cost", Society of Petroleum Engineers, Apr. 11, 2016, doi:10.2118/179702-MS (34 pgs).

Kutus, B. et al., "The Acidity and Self-Catalyzed Lactonization of L-Gulonic Acid: Thermodynamic, Kinetic and Computational Study", Carbohydrate Research 467, 14-22, 2018 (9 pgs).

Schrank, C.L., et al., "Are Quaternary Ammonium Compounds, the Workhorse Disinfectants, Effective against Severe Acute Respiratory Syndrom—Coronavirus—2?", ACS Infect. Dis. 2020, 6, 1553-1557 (5 pgs).

Dubovoy, V, et al., "Synthesis, Characterization, and Antimicrobial Investigation of a Novel Chlorhexidine Cyclamate Complex", Cryst Growth Des., Aug. 5, 2020 (8) (5 pgs).

Zhu, N., et al., "A Novel Coronavirus from Patients with Pneumonia in China, 2019", The New England Journal of Medicine, 382;8, Feb. 20, 2020 (7 pgs).

Isaltis, Inc., Brochure, "Pharmaceutical & Nutraceutical Actives", Sep. 2016 (5 pgs).

Zhang, Z., et al., "Lactonization and Protonation of Gluconic Acid: A Thermodynamic and Kinetic Study by Potentometry, NMR and ESI-MS", Journal of Solution Chemistry, 36(10), Oct. 2007 (26 pgs).

Zeng, P, et al., "Concentration dependent aggregation properties of chlorhexidine salts", International Journal of Pharmaceutics, 367 (2009) (6 pgs).

Zeng, P., et al., "Solubility Properties of Chlorhexidine Salts", Drug Development and Industrial Pharmacy, 35:172-176, 2009 (5 pgs).

Wardman, R., Thesis, "Determination and Removal of Gluconic Acid in Reduced Alcohol Wine and High Acid Grape Juice", Lincoln University, Christchurch, New Zealand, 1995 (121 pgs).

USDA, Technical Evaluation Report, "Chlorhexidine, Livestock", Compiled by Pesticide Research Institute for the USDA National Organic Program, Feb. 12, 2015 (17 pgs).

Tongwen, X., "Electrodialysis processes with bipolar membranes (EDBM) in environmental protection—a review", Resources, Conservation and Recycling 37 (2002) (22 pgs).

Sattar, S.A., "Hierarchy of Susceptibility of Viruses to Environmental Surface Disinfectants: A Predictor of Activity Against New and Emerging Viral Pathogens", Journal of AOAC International, vol. 90, No. 6, 2007 (4 pgs).

Rosen, M.J., et al., "Dynamic Surface Tension of Aqueous Surfactant Solutions", Journal of Colloid and Interface Science, vol. 139, No. 2, Oct. 15, 1990 (11 pgs).

Purdy, K.R., Thesis, "Aspects of chlorhexidine degradation", University of Bath, Bath, England, 1987 (16 pgs).

Pinho, S. P., et al., "Solubility of NaCl, NaBr, and KCl in Water, Methanol, Ethanol, and Their Mixed Solvents", J. Chem. Eng. Data 50, 2005 (4 pgs).

Pereira, B.M.P., et al., "Benzalkonium Chlorides: Uses, Regulatory status, and Microbial Resistance", Applied and Environmental Microbiology, vol. 85, Issue 13, Jul. 2019 (13 pgs).

Park, E., et al., "Silver Nanoparticles Induce Cytotoxicity by a Trojan-Horse Type Mechanism", Toxicology in Vitro 24 (2010) (7 pgs).

Ossowicz, P, et al., "Benzalkonium Salts of Amino Acids—Physicochemical Properties and Anti-Microbial Activity", Tenside Surf. Det. 54 (2017) 6 (11pgs).

Lu, H.J., et al., "Antimicrobial Effects of Weak Acids on the Survival of *Escherichia coli* 0157:H7 under Anaerobic Conditions", Journal of Food Protection, vol. 74 No. 6, 2011 (6 pgs).

Levene, P.A., et al., "Lactone Formation from Mono-and Dicar-Boxylic Sugar Acids", from the Laboratories of The Rockefeller Institute for Medical Research, Jun. 1, 1925 (17 pgs).

Levene, P.A., et al., "Lactone Formation from Gluconic Acids and the Structure of Glucose", from the Laboratories of The Rockefeller Institute for Medical Research, Apr. 21, 1926 (13 pgs).

Kutus, B., et al., "The acidity and self-catalyzed lactonization of L-gulonic acid: Thermodynamic, kinetic and computational study", Carbohydrate Research 467 (2018) (9 pgs).

Jaiswal, S., et al., "Enhancement of the antibacterial properties of silver nanoparticles using B-cyclodextrin as a capping agent", International Journal of Antimicrobial Agents 36 (2010) (4 pgs).

Hua, X.Y., et al., "Dynamic Surface Tension of Aqueous Surfactant Solutions", Journal of Colloid and Interface Science, vol. 124, No. 2, Aug. 1988 (8 pgs).

Heard, D. D., et al., "The colloidal properties of chlorhexidine and its interaction with some macromolecules", J. Pharm. Pharmac., vol. 20, No. 7, 1968 (8 pgs).

Golin, A.P., et al., "Hand sanitizers: A review of ingredients, mechanisms of action, modes of delivery, and efficacy against coronaviruses", American Journal of Infection Control, 48 (2020) (7 pgs).

(56) References Cited

OTHER PUBLICATIONS

Georgiev, G.A., et al., "Surface Chemistry Study of the Interactions of Benzalkonium Chloride with Films of Meibum, Corneal Cells Lipids, and Whole Tears", IOVS, Jun. 2011, vol. 52, No. 7 (10 pgs).
Book, European Pharmacopoeia 7.0, "Chlorhexidine digluconate solution", 2021, pp. 1660-1662 (3 pgs).
Letter of acceptance from the United States Environmental Protection Agency dated Jun. 1, 2020 and the Application for Pesticide Notification under Pesticide Registration Notice 98-10 for Lysol Brand Disinfectant S.A. Cleaner (17 pgs).
Letter of acceptance from the United States Environmental Protection Agency dated May 5, 2020 and the Application for amended label under the Federal Insecticide, Fungicide and Rodenticide Act, as amended for Glyclean Hard Surface Cleaner(8 pgs).
Letter of acceptance from the United States Environmental Protection Agency dated Feb. 18, 2015 and the Application for amended label under the Federal Insecticide, Fungicide and Rodenticide Act, as amended for WC Complete (11 pgs).
Berge, S.M., et al., "Pharmaceutical Salts", Journal of Pharmaceutical Sciences, vol. 66, No. 1, Jan. 1977 (19 pgs).
ASTM International Designation: E2315-16, "Standard Guide for Assessment of Antimicrobial Activity Using a Time-Kill Procedure", 2021 (5 pgs).
Asano, T., "Effects of Gluconic Acid on Human Faecal Bacteria", Microbial Ecology in Health and Disease, 7:5, 1994 (11 pgs).
Letter from the United States Environmental Protection Agency, PR Notice 88-2 dated Feb. 26, 1988, "Clustering pf Quaternary Ammonium Compounds" (6 pgs).
Product Sheet, Dow, "Dowex Marathon MSC" (Date ??? ) (2 pgs).
Yu, J., et al., "Preparation, characterization, and antibacterial property of carboxymethyl cellulose derivatives bearing tetrabutylammonium salt", International Journal of Biological Macromolecules, vol. 176, Apr. 15, 2021 (6 pgs).

* cited by examiner

ANTIMICROBIAL COMPOUNDS BASED ON GLUCOHEPTONIC ACIDS AND THEIR SALTS

CROSS REFERENCE TO RELATED APPLICATIONS

This application claims priority to and the benefit of Provisional Application Ser. No. 63/133,440, filed Jan. 4, 2021, which is incorporated herein by reference in its entirety for all relevant purposes.

FIELD OF THE INVENTION

Provided herein are methods for disinfecting or sanitizing. Also provided herein are methods for the preparation of certain compounds useful as a disinfectant or sanitizer, such as glucoheptonic acid, chlorhexidine diglucoheptonate, benzalkonium glucoheptonate, and combinations thereof. Still further provided herein are methods for evaluating a compound for performance in microbial disinfecting or sanitizing.

BACKGROUND TO THE INVENTION

Chlorhexidine is a compound used in the medical field and in dentistry as an oral disinfectant. Benzalkonium chloride has been traditionally used in a variety of products, including laundry fabric softeners, shampoos, hair conditioners, and other personal care products. Benzalkonium chloride may also be found in a variety of pharmaceutical products such as eye, ear, or nasal drops. However, it is believed that certain microbes are beginning to develop resistance and/or tolerance to benzalkonium chloride.

There remains a need in the art to develop disinfecting or sanitizing compounds effective against a growing number of novel viruses, such as SARS-COV-2. In connection with the growing number of novel viruses, there is also a need to develop new disinfecting or sanitizing compounds including more effective benzalkonium salts that reduce microbial populations effectively and are not prone to microbe resistance. Still further, there is a need to improve the process of making the feedstocks for preparing such new disinfecting or sanitizing compounds.

SUMMARY OF THE INVENTION

One aspect of the present invention is a method of disinfecting or sanitizing. The method comprises contacting an aqueous composition comprising a component selected from the group consisting of glucoheptonic acid, chlorhexidine diglucoheptonate, benzalkonium glucoheptonate, and combinations thereof with a microbial population. The Log Reduction is about 3 or greater, 30 seconds after application.

Another aspect of the present invention is directed to a method of preparing glucoheptonic acid. The method comprises dissolving a glucoheptonate salt in water to form a solution; combining the solution with an acidic ion exchange resin to form a slurry; filtering the slurry to remove the ion exchange resin, and produce glucoheptonic acid. Optionally, the liquid from the filtered slurry may be dried to form the glucoheptonic acid. The conversion of the glucoheptonate salt to glucoheptonic acid is about 99% or greater, about 99.1% or greater, about 99.2% or greater, about 99.3% or greater, about 99.4% or greater, or about 99.5% or greater.

A further aspect of the present invention is directed to a method of preparing a benzalkonium glucoheptonate. The method comprises combining a benzalkonium salt and a glucoheptonate salt in a container and stirring the combination. Optionally, the combination is heated to a temperature of about 90° C. or greater. Optionally, the combination is subjected to a nitrogen purge step during at least a portion of the heating.

An additional aspect of the present invention is directed to a method of evaluating a compound for performance in microbial disinfecting or sanitizing. The method comprises conducting a Bubble Pressure Tensiometry test of a compound; evaluating the reduction in surface tension exhibited by a compound as a function of time; and comparing the surface tension reduction to a compound known to exhibit microbial disinfecting or sanitizing properties to determine if the tested compound is useful for microbial disinfecting or sanitizing.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE INVENTION

Figure 1:
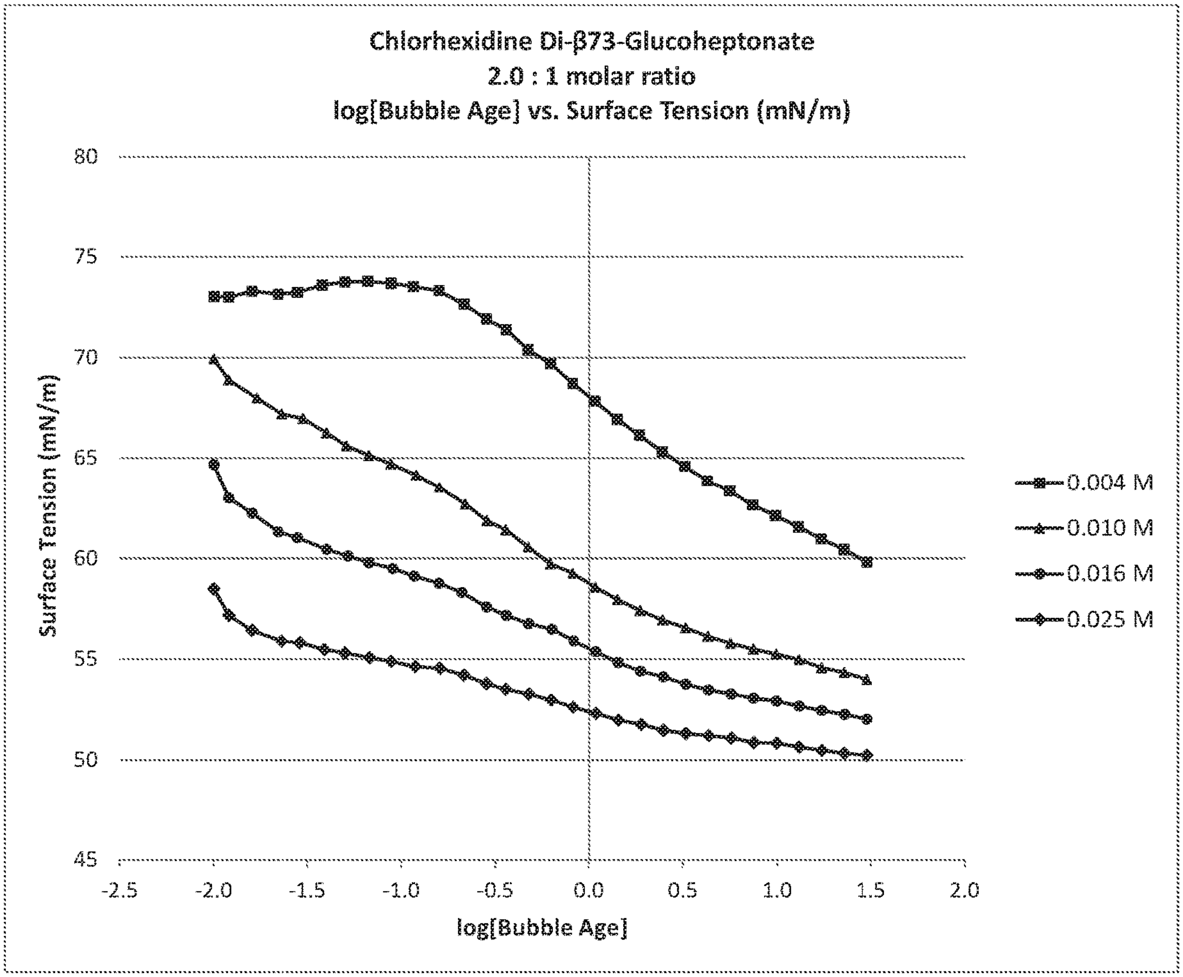
FIG. 1 presents a comparison of the bubble age to surface tension for RM14A at various concentrations.

In accordance with the present invention, methods for disinfecting or sanitizing have been devised that utilize disinfecting or sanitizing components previously not known to exhibit such properties and/or having surprising improvements over similar compounds. In particular, the methods of the present invention of disinfecting or sanitizing comprise contacting an aqueous composition comprising a component selected from the group consisting of glucoheptonic acid, chlorhexidine diglucoheptonate, benzalkonium glucoheptonate, and combinations thereof with a microbial population. Generally, contact with one or more of these components achieves a Log Reduction 30 seconds after application that is about 3 or greater.

Processes of the present invention are also directed to the use of diglucoheptonate salts having a certain concentration of α or β forms. Such processes include, for example, the use of an aqueous composition comprising chlorhexidine di-α-glucoheptonate and chlorhexidine di-β-glucoheptonate wherein the composition comprises a chlorhexidine di-α-glucoheptonate concentration, based on total isomers of chlorhexidine diglucoheptonate, of about 90% or greater. Alternatively, the microbial population is contacted with an aqueous composition comprising chlorhexidine di-α-glucoheptonate and chlorhexidine di-β-glucoheptonate wherein the composition comprises a chlorhexidine di-β-glucoheptonate concentration, based on total isomers of chlorhexidine diglucoheptonate, of about 25% or greater.

The present invention is further directed to methods of preparing glucoheptonic acid. The method provides improved conversion rates using a process that is less complex than previously used electrodialysis processes. The methods generally comprise dissolving a glucoheptonate salt in water to form a solution combining the solution with an acidic ion exchange resin to form a slurry; and filtering the ion exchange resin from the slurry to form glucoheptonic acid. Optionally, the liquid from the filtered slurry may be dried to form the glucoheptonic acid. The method achieves a conversion of the glucoheptonate salt to glucoheptonic acid of about 99% or greater, about 99.1% or greater, about 99.2% or greater, about 99.3% or greater, about 99.4% or greater, or about 99.5% or greater.

Still further, the present invention is directed to methods of preparing chlorhexidine diglucoheptonates using the glucoheptonic acid prepared in this manner. The process comprises combining chlorhexidine and water to form a slurry, adding the glucoheptonic acid to the slurry, and mixing the combination until the glucoheptonic acid is dissolved.

The present invention is also directed to methods of preparing a benzalkonium glucoheptonate. The method comprises combining a benzalkonium salt and a glucoheptonate salt in a container and stirring the combination. Optionally, the combination is heated to a temperature of about 90° C. or greater. Optionally, the combination is subjected to a nitrogen purge step during at least a portion of the heating.

Further, the present invention is directed to methods of evaluating a compound for performance in microbial disinfecting or sanitizing. The method comprises conducting a Bubble Pressure Tensiometry test of a compound; evaluating the reduction in surface tension exhibited by a compound as a function of time; and comparing the surface tension reduction to a compound known to exhibit microbial disinfecting or sanitizing properties to determine if the tested compound is useful for microbial disinfecting or sanitizing.

In one embodiment of the present invention, a process for preparing a glucoheptonate salt generally comprises the reaction of a glucoheptonic acid with a free base in the reaction scheme set forth below. An example of such a reaction is the reaction of chlorhexidine with glucoheptonic acid to produce chlorhexidine diglucoheptonate.

$$B{:}+\text{Glucoheptonic Acid}\rightarrow[BH]+[\text{Glucoheptonate}]^{-}$$

Still further embodiments of the present invention are directed to reacting a glucoheptonate salt with a quaternary ammonium salt to form a desired benzalkonium glucoheptonate salt. For example, reaction of a benzalkonium salt with sodium glucoheptonate.

Quaternary ammonium compounds (QAC's) are known to be effective as virucides. However, the growing preference in the global marketplace is to prepare at least a portion of such compounds from renewable resources in efforts to improve resource sustainability and reduce reliance on petrochemical feedstocks. One particular aspect of the present invention is directed to processes for preparing the quaternary ammonium salt, benzalkonium glucoheptonate from non-petrochemical components. For example, the benzalkonium component may be prepared from either coconut oil or palm kernel oil based amines, while the glucoheptonate portion of the molecule may be prepared from natural sugars that include glucose.

While particular quaternary ammonium compounds are discussed herein, it should be understood that the processes described herein are applicable to a wider variety of quaternary compounds, particularly where the quaternary ammonium components are paired with polyhydroxycarboxylic acids, using the free acid or salt form.

Still further aspects of the present invention are directed to use of the glucoheptonate salts or acids described herein for the destruction of certain undesirable microbes. For example, the destruction of yeast/fungi, viruses, bacteria, etc.

Glucoheptonate salts (e.g., sodium glucoheptonate) may be prepared from a variety of saccharide sources. For example, glucose, corn syrup, molasses, molasses bottoms, black strap molasses, and combinations thereof. Generally, glucoheptonate is formed as the reaction product between a sugar and cyanide. For example, sodium cyanide.

In one embodiment, sodium glucoheptonate is formed by reacting glucose and sodium cyanide. Sodium cyanide is reacted with an approximately equimolar quantity of glucose at a temperature of 0-60° C., under mildly alkaline conditions over a several hour period. Ammonia is a byproduct of this reaction and is removed during the course of the reaction. When glucose is used to produce sodium glucoheptonate, the resulting aqueous product is composed of two glucoheptonates, in their α- and β-isomeric forms. The general reaction scheme of glucose to sodium glucoheptonate is set forth below.

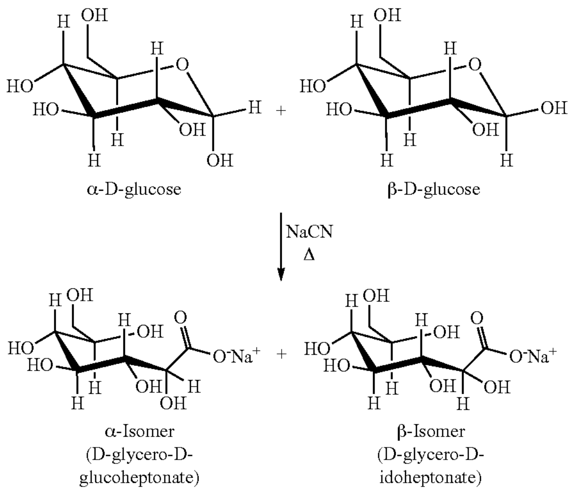

α-D-glucose

β-D-glucose

α-Isomer (D-glycero-D-glucoheptonate)

β-Isomer (D-glycero-D-idoheptonate)

In certain embodiments, the resulting mother liquor of the reaction is reduced in volume, cooled, and a lightly colored α-glucoheptonate salt (e.g., sodium α-glucoheptonate) is precipitated from the liquor. Through this precipitation process it is possible to form a solid having a purity of the α-isomer of greater than 99%. Following the precipitation step, the remaining liquor is a mixture of both α- and β-isomer, having a majority β-isomer product. This remaining liquor containing a mixture of both isomers is generally darker in appearance.

Preparing Glucoheptonic Acid

After the saccharide has been converted to a glucoheptonate salt (e.g., sodium glucoheptonate), the salt may be converted to glucoheptonic acid. One method of the present invention is directed to preparing glucoheptonic acid using an ion exchange resin. Although discussed below in the context of a sodium glucoheptonate process, it is understood that similar processes may be employed with other glucoheptonate salts.

Previously known procedures for the conversion of a glucoheptonate salt to a glucoheptonic acid comprised the use of an electrodialysis system. However, use of such a process requires significant capital expenditure and processing costs. Further, such systems typically exhibit yields of about 98%. In contrast, the inventors have discovered that use of an ion exchange resin as described herein presents a simpler process for the conversion and results in conversion rates of up to 99% or greater. In the ion exchange process of the present invention, for sodium α-glucoheptonate samples, it was found by sodium ion analysis that the conversion was >99.3% effective. For sodium β-glucoheptonate samples, it was found that the conversion was >99.1% effective. This additional conversion rate is significant when attempting to produce commercial scale quantities of the glucoheptonic acid.

In one process of the present invention, sodium glucoheptonate is contacted with an acidic ion exchange resin to convert the sodium salt to glucoheptonic acid. An acid ion exchange resin (as a water/resin slurry) is loaded into a flash chromatography column at ambient temperature. Sodium glucoheptonate is then dissolved in water, loaded into the column, and the column is eluted with water. The resulting eluate comprises a solution of glucoheptonic acid. Various iterations of this process may be conducted with different glucoheptonate salts. For example, in one embodiment, sodium α-glucoheptonate may be introduced into the column to produce a solution of α-glucoheptonic acid. In another embodiment, a sodium β73-glucoheptonate solution may be introduced into the column to produce a β73-glucoheptonic acid solution. The resulting glucoheptonic acid may be optionally dried in a forced air oven. The sodium β73-glucoheptonate solution is a solution of sodium glucoheptonate comprising from about 60% to about 75% β-isomer. For example, from about 61% to about 74%, from about 61% to about 73%, from about 61% to about 72%, from about 61% to about 71%, from about 62% to about 71%, from about 63% to about 71%, from about 64% to about 71%, from about 65% to about 71%, from about 66% to about 71%, from about 67% to about 71%, from about 68% to about 71%, or from about 69% to about 71% of the β-isomer. In certain embodiments, the sodium β73-glucoheptonate solution comprises about 67-71% β-isomer and about 29-33% α isomer. In another embodiment, the sodium 73-glucoheptonate solution comprises about 61-73.5% β-isomer and about 26.5-39% α isomer. In some embodiments, the sodium β73-glucoheptonate solution is a solution having a typical ratio of α to β isomer, having a relative absence of borate, and having a low solids content. For example, in some embodiments, the sodium β73-glucoheptonate solution has a solids content at room temperature of about 20 wt. % or less, about 15 wt. % or less, about 10 wt. % or less, about 5 wt. % or less, or about 1 wt. % or less.

In another process of the present invention, sodium glucoheptonate is dissolved in water in a first container. An acidic ion exchange resin is then added to the first container to form a slurry. The slurry is mixed by pouring the combination between a first and a second container (e.g. from the first container to a second container, from the second container to the first container, etc.) at 20 minute intervals for a period of four hours. The resulting mixed slurry is then filtered to remove the ion exchange resin and yield a solution of glucoheptonic acid. The process of pouring the combination between a first and a second container may be untaken at a variety of intervals. For example, at 5 minute intervals for a period of at least about 30 minutes, 5 minute intervals for a period of at least about 1 hour, 10 minute intervals for a period of at least about 1 hour, 10 minute intervals for a period of at least about 2 hours, 10 minute intervals for a period of at least about 3 hours, 10 minute intervals for a period of at least about 4 hours, 15 minute intervals for a period of at least about 4 hours, 20 minute intervals for a period of at least about 4 hours, or 20 minute intervals for a period of at least about 5 hours.

This process may be conducted with various glucoheptonate salts. For example, in one embodiment, sodium α-glucoheptonate (i.e. a solution comprising less than 1% of the β isomer of sodium glucoheptonate) is combined with the ion exchange resin to produce a slurry of α-glucoheptonic acid after mixing between a first and a second container as described above. The resulting α-glucoheptonic acid is optionally dried in a forced air oven (e.g., at a temperature of about 65° C.) to form a film. After drying, in certain embodiments, the α-glucoheptonic acid concentration based on total isomers is about 90% or greater, as determined by HPLC. In other embodiments, the α-glucoheptonic acid concentration based on total isomers is about 95% or greater, about 96% or greater, about 97% or greater, about 98% or greater, about 99% or greater, about 99.5% or greater, or about 99.9% or greater.

In another embodiment, a sodium β73-glucoheptonate solution is combined with an ion exchange resin to produce a slurry of β73-glucoheptonic acid after mixing between a first and a second container as described above. The resulting glucoheptonic acid is optionally dried in a forced air oven (e.g., at a temperature of about 65° C.) to form a film. After drying, in certain embodiments, the ratio of β-glucoheptonic acid to α-glucoheptonic acid may be 2.61 (73.2% β isomer) as determined by HPLC. In other embodiments, the ratio of β-glucoheptonic acid to α-glucoheptonic acid may be about 1.5 or greater, about 2.0 or greater, about 2.5 or greater, about 3.0 or greater, about 3.5 or greater about 4.0 or greater, or about 4.5 or greater.

The ion exchange resin used in the process of the present invention to convert a glucoheptonate salt to glucoheptonic acid may be any resin suitable for such a conversion. In certain embodiments, the ion exchange resin is an acidic resin. For example, a strong acid cation type resin. In one embodiments, the strong acid cation exchange resin has a sulfonic acid functional group. Without being bound by the theory, it is believed that the presence of a strong acid functional group aids in the more complete conversion of a glucoheptonate salt to glucoheptonic acid. In certain other embodiments, the ion exchange resin comprises a styrene-divinyl benzene matrix.

In various embodiments, the ion exchange resin has a degree of crosslinking from about 1% to about 25%. For example, from about 2% to about 25%, from about 2% to about 20%, from about 2% to about 19%, from about 2% to about 18%, from about 2% to about 17%, from about 2% to about 16%, from about 4% to about 16%, from about 4% to about 14%, from about 4% to about 12%, from about 4% to about 10%, from about 4% to about 9%, from about 5% to about 9%, from about 6% to about 9%, or from about 7% to about 9%. In some embodiments, the ion exchange resin has a degree of crosslinking of about 1% or greater, about 2% or greater, about 3% or greater, about 4% or greater, or about 5% or greater.

embodiment, the ion exchange resin is a LEWATIT MONOPLUS SP 112 H series cation exchange resin.

Preparing a Chlorhexidine Salt

In processes of the present invention, the glucoheptonic acid may be reacted with a base in order to prepare the desired glucoheptonate compound.

In certain processes of the present invention, glucoheptonic acid is reacted with chlorhexidine in order to prepare the desired chlorhexidine glucoheptonate compound.

Other aspects of the present invention are directed to the formation and use of chlorhexidine diglucoheptonate salts. As set forth in the general reaction scheme below, chlorhexidine is reacted with glucoheptonic acid to form chlorhexidine diglucoheptonate.

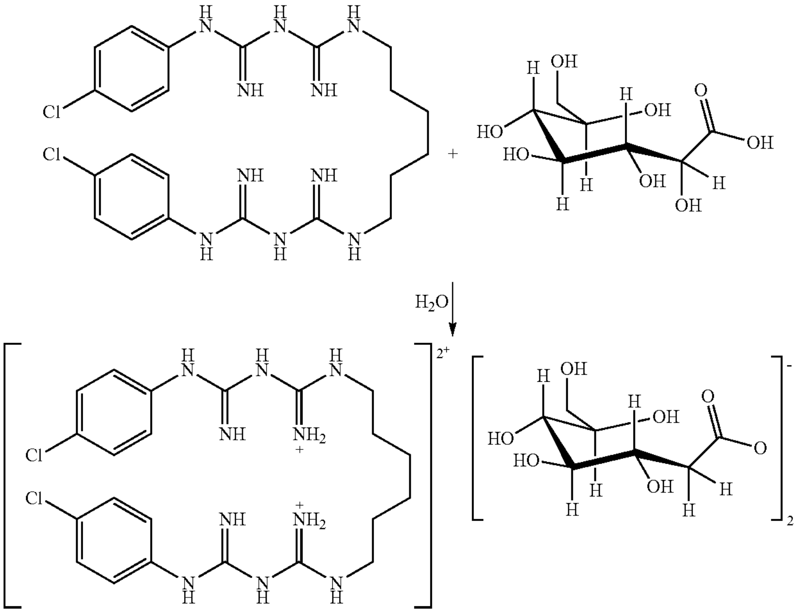

In certain embodiments, the ion exchange resin is macroporous.

In some embodiments the ion exchange resin has a mean particle size of from about 300 μm to about 700 μm, from about 350 μm to about 700 μm, from about 375 μm to about 700 μm, from about 400 μm to about 700 μm, from about 400 μm to about 675 μm, from about 400 μm to about 650 μm, from about 400 μm to about 625 μm, from about 400 μm to about 600 μm, from about 425 μm to about 600 μm, from about 450 μm to about 600 μm, from about 475 μm to about 600 μm, from about 500 μm to about 600 μm, from about 525 μm to about 600 μm, or from about 550 μm to about 600 μm. In certain other embodiments, the ion exchange resin has a mean particle size of from about 400 μm to about 900 μm, from about 450 μm to about 900 μm, from about 500 μm to about 900 μm, from about 550 μm to about 900 μm, from about 600 μm to about 900 μm, from about 600 μm to about 850 μm, from about 600 μm to about 800 μm, from about 600 μm to about 750 μm, or from about 650 μm to about 700 μm.

In various embodiments, the ion exchange resin comprises monodisperse ion exchange particles (e.g., beads).

In one embodiment, the ion exchange resin is a DOWEX MARATHON MSC series cation exchange resin. In another In certain embodiments, the chlorhexidine diglucoheptonate of the present invention is prepared be reacting a glucoheptonic acid with chlorhexidine, wherein the process comprises a molar excess of the glucoheptonic acid. In certain embodiments, the chlorhexidine diglucoheptonate of the present invention has a molar ratio of glucoheptonic acid to chlorhexidine of from about 1.5:1 to about 3:1, from about 2:1 to about 2.9:1, from about 2:1 to about 2.8:1, from about 2:1 to about 2.7:1, from about 2:1 to about 2.6:1, or from about 2.1:1 to about 2.6:1. In other embodiments, the chlorhexidine diglucoheptonate of the present invention has a molar ratio of glucoheptonic acid to chlorhexidine of from about 1:1 to about 5:1, from about 1:1 to about 4:1, from about 1:1 to about 3:1, from about 1:1 to about 2.5:1, from about 1:1 to about 2.0:1, from about 1:1 to about 1.9:1, from about 1:1 to about 1.8:1, from about 1:1 to about 1.7:1, from about 1:1 to about 1.6:1, or from about 1:1 to about 1.5:1.

Preparing a Benzalkonium Salt

In other embodiments, it may be more economical to utilize a counterion in the form of a salt, instead of a base. For example, unlike the free base chlorhexidine, benzalkonium chloride is a salt and presents difficulties in preparing alternate salts. Thus, where it is desired to form a benzalkonium glucoheptonate, it is preferred to react a benzalkonium salt with a glucoheptonate salt. For example, the benzalkonium salt may be benzalkonium chloride and the glucoheptonate salt may be sodium glucoheptonate.

The benzalkonium chloride used in exemplary embodiments of the present invention is generally formed by the reaction scheme set forth below, wherein R is 40% $C_{12}$, 50% $C_{14}$, and 10% $C_{16}$.

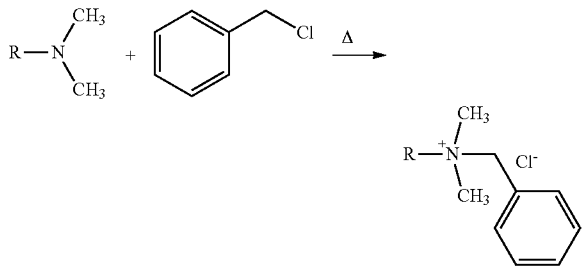

Generally, the reaction of a benzalkonium salt with a glucoheptonate salt comprises combining the two com- 1. Ion exchange purification of one or both of the benzalkonium and glucoheptonic streams prior to mixing (aqueous).
2. Mixing the benzalkonium and glucoheptonic streams without a solvent, and then subsequently drying the medium, with or without vacuum.
3. Mixing the benzalkonium and glucoheptonic streams in a suitable solvent, and subsequently drying the mixture.
4. Centrifugation, precipitation, and/or filtration.
5. Solvent removal.
6. Drying.
7. Concentration of the benzalkonium glucoheptonate salt by removal of liquid through heating.
8. Dialysis.
9. Electrodialysis.
10. Ion exchange purification of the benzalkonium glucoheptonate salt product.

For example, in one embodiment of the present invention, benzalkonium glucoheptonate is formed by the reaction scheme below, utilizing one or more of the optional processing steps set forth above.

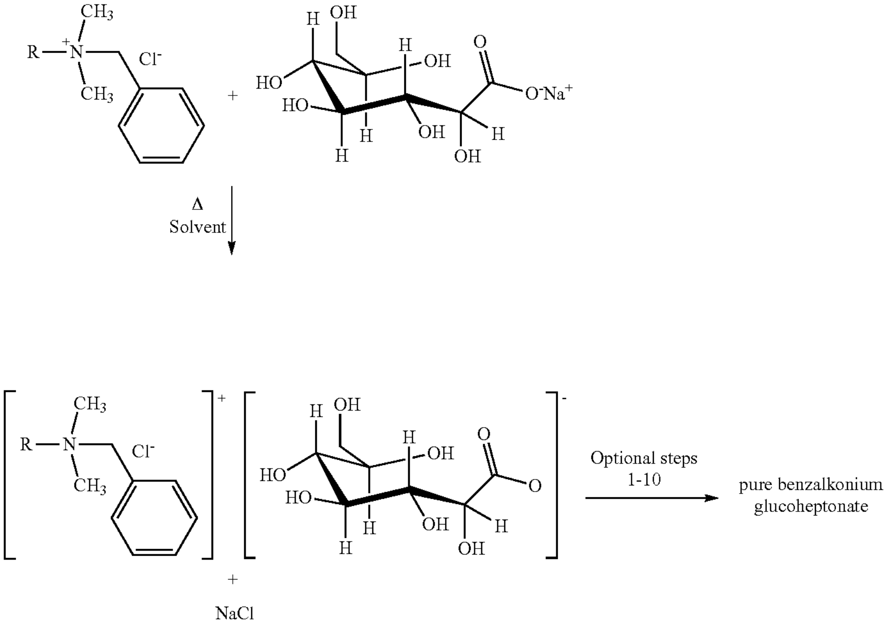

pounds in a container and mixing. Optionally, the temperature of the combination may be increased (e.g., to about 90° C.). Optionally, the process may further comprise the use of a nitrogen purge to remove excess moisture.

One challenge presented by the proposed process of reacting a benzalkonium salt with a glucoheptonate salt is that the reaction yields a stoichiometric amount of a metal salt. Since the virucidal action of benzalkonium glucoheptonate relies on formation of an ion pair between the polyhydroxycarboxylate anion and the quaternary ammonium cation, the additional equivalent of metal salt must be removed. Therefore, it may be required to conduct one or more of the following process steps prior to, during, or after the reaction of the benzalkonium salt (benzalkonium chloride) with the glucoheptonate salt:

Any suitable solvent useful for forming benzalkonium glucoheptonate may be used in the above reaction. For example, the solvent may be selected from the group consisting of methanol, ethanol, isopropyl alcohol, n-propyl alcohol, acetone, butyl alcohol, and combinations thereof. Butyl alcohol should be understood to include one or more of n-butanol, sec-butanol, isobutanol and tert-butanol.

In certain embodiments, the benzalkonium glucoheptonate of the present invention is prepared be reacting a benzalkonium salt with a glucoheptonate salt, wherein the process comprises a molar excess of the glucoheptonate salt. For example, in one embodiment, the molar ratio of glucoheptonate salt to benzalkonium salt is from about 1:1 to about 5:1, from about 1:1 to about 4:1, from about 1:1 to about 3:1, from about 1:1 to about 2.5:1, from about 1:1 to about 2.0:1, from about 1:1 to about 1.9:1, from about 1:1 to about 1.8:1, from about 1:1 to about 1.7:1, from about 1:1 to about 1.6:1, or from about 1:1 to about 1.5:1. In certain other embodiments, the molar ratio of glucoheptonate salt to benzalkonium salt is from about 1.1:1 to about 5:1, from about 1.1:1 to about 4:1, from about 1.1:1 to about 3:1, from about 1.1:1 to about 2.5:1, from about 1.1:1 to about 2.0:1, from about 1.1:1 to about 1.9:1, from about 1.1:1 to about 1.8:1, from about 1.1:1 to about 1.7:1, from about 1.1:1 to about 1.6:1, or from about 1.1:1 to about 1.5:1.

While the specific example of benzalkonium glucoheptonate has been provided herein, there are many other compounds that may be prepared with similar expectations of efficacy. The benzalkonium counterion described herein is an example of a broader class of cationics. Therefore, other suitable sources of cationic counterions may include, but are not necessarily limited to, benzethonium chloride, polymeric quaternary ammonium salts, dialkyldimethyl quaternary ammonium salts, dialkylmethyl ammonium quaternary ammonium salts with twin tails, other alkyl or hydroxyalkyl substituted quaternary ammonium salts, cetylpyridinium chloride, benzyl substituted quaternary ammonium salts, picolinium salts, imidazolinium salts, N-ethyl-Morpholinium salts, isoquinolinium salts, chlorhexidine salts, and combinations thereof. The aforementioned sources of cationic counterions may be used to prepare glucoheptonate compounds that are expected to exhibit similar efficacy, for example by reacting the aforementioned cationic counterions with a glucoheptonate salt.

For example, the glucoheptonate compound may be selected from the group consisting of benzethonium glucoheptonate, polymeric quaternary ammonium glucoheptonates, and cetylpyridinium glucoheptonate.

In certain embodiments, the glucoheptonate compound may be a quaternary ammonium salt having the formula: $R_1R_2R_3R_4N^+X^-$, wherein $R_1$ and $R_2$ are independently selected from the group consisting of straight, branched, or cyclic alkyl or alkenyl groups having from about 8 to about 18 carbon atoms, and $R_3$ and $R_4$ are independently selected from the group consisting of straight alkyl groups having from about 1 to about 4 carbon atoms, hydroxyethyl, hydroxypropyl, hydroxybutyl, $-(CH_2CH_2O)_mCH_2CH_2OH$, $-(CH_2CHCH_3O)_mCH_2CHCH_3OH$, $-(CH_2CH_2O)_m(CH_2CHCH_3O)_nCH_2CHCH_3OH$, or $-(CH_2CHCH_3O)_m(CH_2CH_2O)_nCH_2CH_2OH$, wherein m is an integer from about 1 to about 10 and n is an integer from about 1 to about 10, and $X^-$ is glucoheptonate.

In certain embodiments, the glucoheptonate compound may be a quaternary ammonium salt having the formula: $R_1R_2R_3R_4N^+X^-$, wherein $R_1$ is selected from the group consisting of 3-alkoxy-2-hydroxypropyl or a straight, branched, or cyclic alkyl or alkenyl group having from about 8 to about 18 carbon atoms, $R_2$, $R_3$ and $R_4$ are independently selected from the group consisting of straight alkyl groups having from about 1 to about 4 carbon atoms, hydroxyethyl, hydroxypropyl, hydroxybutyl, $-(CH_2CH_2O)_mCH_2CH_2OH$, $-(CH_2CHCH_3O)_mCH_2CHCH_3OH$, $-(CH_2CH_2O)_m(CH_2CHCH_3O)_nCH_2CHCH_3OH$, or $-(CH_2CHCH_3O)_m(CH_2CH_2O)_nCH_2CH_2OH$, wherein m is an integer from about 1 to about 10 and n is an integer from about 1 to about 10, and $X^-$ is glucoheptonate.

In another embodiment, the glucoheptonate compound may be a quaternary ammonium salt having the formula: $R_1R_2R_3R_4N^+X^-$, wherein $R_1$ is selected from the group consisting of a straight, branched, or cyclic alkyl or alkenyl group having from about 8 to about 18 carbon atoms, $R_2$ is selected from the group consisting of a substituted or unsubstituted benzyl, ethylbenzyl, naphthyl, or methylnaphthyl, and $R_3$ and $R_4$ are independently selected from the group consisting of straight alkyl groups having from about 1 to about 4 carbon atoms, hydroxyethyl, hydroxypropyl, hydroxybutyl, $-(CH_2CH_2O)_mCH_2CH_2OH$, $-(CH_2CHCH_3O)_mCH_2CHCH_3OH$, $-(CH_2CH_2O)_m(CH_2CHCH_3O)_nCH_2CHCH_3OH$, or $-(CH_2CHCH_3O)_m(CH_2CH_2O)_nCH_2CH_2OH$, wherein m is an integer from about 1 to about 10 and n is an integer from about 1 to about 10, and $X^-$ is glucoheptonate.

In yet another embodiment, the glucoheptonate compound may be a quaternary ammonium salt having the formula $R_1R_2R_3R_4N^+X^-$, wherein $R_1$ is selected from the group consisting of 3-alkoxy-2-hydroxypropyl or a straight, branched, or cyclic alkyl or alkenyl group having from about 8 to about 18 carbon atoms, $R_2$ is selected from the group consisting of a substituted or unsubstituted benzyl, ethylbenzyl, naphthyl, or methylnaphthyl, a straight, branched, or cyclic alkyl or alkenyl group having from about 8 to about 18 carbon atoms, a straight alkyl group having from about 1 to about 4 carbon atoms, hydroxyethyl, hydroxypropyl, hydroxy butyl, $-(CH_2CH_2O)_mCH_2CH_2OH$, $-(CH_2CHCH_3O)_mCH_2CHCH_3OH$, $-(CH_2CH_2O)_m(CH_2CHCH_3O)_nCH_2CHCH_3OH$, or $-(CH_2CHCH_3O)_m(CH_2CH_2O)_nCH_2CH_2OH$, wherein m is an integer from about 1 to about 10, n is an integer from about 1 to about 10, $R_3$ and $R_4$ are independently selected from the group consisting of a straight alkyl group having from about 1 to about 4 carbon atoms, hydroxyethyl, hydroxypropyl, hydroxybutyl, $-(CH_2CH_2O)_mCH_2CH_2OH$, $-(CH_2CHCH_3O)_mCH_2CHCH_3OH$, $-(CH_2CH_2O)_m(CH_2CHCH_3O)_nCH_2CHCH_3OH$, or $-(CH_2CHCH_3O)_m(CH_2CH_2O)_nCH_2CH_2OH$, where m is an integer from about 1 to about 10 and n is an integer from about 1 to about 10, and $X^-$ is glucoheptonate.

For example, in some embodiments, the glucoheptonate compound may be selected from the following, wherein $X^-$ is glucoheptonate:

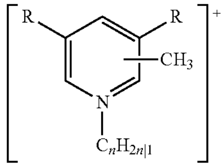

$X^-$,

R = $C_2H_5$ or H
n = 12-16

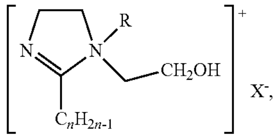

$X^-$,

R = H,
R = $CH_2Ph$,
R = $CH_2CH_2CH_2CH_2Cl$
n = 8-18

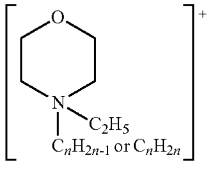

$X^-$, n = 14-18

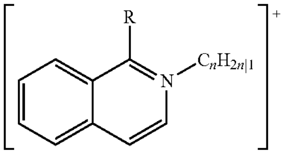

$X^-$, and

R = H or $CH_3$
n = 12-18

-continued

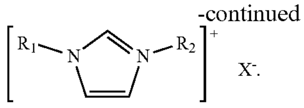

$R_1 = C_{1\text{-}4}$ alkyl
$R_2 = C_{8\text{-}18}$ alkyl or alkenyl

Applications of Glucoheptonate Compounds

The glucoheptonate compounds disclosed herein may be useful as antimicrobials or virucides. Such glucoheptonate compounds include, for example, glucoheptonic acid, chlorhexidine diglucoheptonate, benzalkonium glucoheptonate, and combinations thereof. The glucoheptonate compounds may be present in a composition in an amount sufficient to achieve the desired antimicrobial or virucidal effects. For example, it may be desirable to form a composition having a certain minimum inhibitory concentration (MIC), defined as the lowest concentration of an antimicrobial that will inhibit the visible growth of a microorganism after overnight incubation. In other embodiments, it may be desirable to form a composition having a certain minimum bactericidal concentration (MBC), defined as the lowest concentration of antimicrobial that will prevent the growth of an organism. In still other embodiments, it may be desirable to form a composition having a concentration suitable for achieving a certain Log Reduction (e.g., Log 3 Reduction after 30 seconds).

In certain embodiments, glucoheptonic acid is present in a composition comprising from about 0.5 to about 10 wt %, from about 0.5 to about 9 wt %, from about 0.5 to about 8 wt %, from about 0.5 to about 7 wt %, from about 0.5 to about 6 wt %, from about 0.6 to about 6 wt %, from about 0.7 to about 6 wt %, from about 0.8 to about 6 wt %, from about 0.9 to about 6 wt %, from about 1 to about 6 wt %, from about 2 to about 6 wt %, from about 3 to about 6 wt %, from about 4 to about 6 wt %, or from about 5 to about 6 wt % of glucoheptonic acid.

In one embodiment, chlorhexidine diglucoheptonate is present in a composition comprising from about 0.005 to about 10 wt %, from about 0.005 to about 9 wt %, from about 0.005 to about 8 wt %, from about 0.005 to about 7 wt %, from about 0.005 to about 6 wt %, from about 0.006 to about 6 wt %, from about 0.007 to about 6 wt %, from about 0.008 to about 6 wt %, from about 0.009 to about 6 wt %, from about 0.01 to about 6 wt %, from about 0.011 to about 6 wt %, from about 0.012 to about 6 wt %, from about 0.013 to about 6 wt %, from about 0.014 to about 6 wt %, from about 0.015 to about 6 wt %, or from about 0.015 to about 5 wt % of chlorhexidine diglucoheptonate.

In some embodiments, benzalkonium glucoheptonate is present in a composition comprising from about 0.00025 to about 10 wt %, from about 0.0005 to about 10 wt %, from about 0.0005 to about 9 wt %, from about 0.0005 to about 8 wt %, from about 0.0005 to about 7 wt %, from about 0.0005 to about 6 wt %, from about 0.0005 to about 5 wt %, from about 0.0005 to about 4 wt %, from about 0.001 to about 4 wt %, from about 0.002 to about 4 wt %, from about 0.003 to about 4 wt %, from about 0.004 to about 4 wt %, from about 0.005 to about 4 wt %, from about 0.01 to about 4 wt %, from about 0.02 to about 4 wt %, from about 0.04 to about 4 wt %, from about 0.06 to about 4 wt %, from about 0.08 to about 4 wt %, or from about 0.10 to about 4 wt % of benzalkonium glucoheptonate.

Preparing the glucoheptonate compound from raw materials such as those described above (e.g., glucose) allows for the production of an antimicrobial compound having a desirable renewable carbon index. The glucoheptonate compounds have, for example, a renewable carbon index of about 50% or greater, about 55% or greater, about 60% or greater, about 65% or greater, about 70% or greater, about 75% or greater, about 80% or greater, about 85% or greater, about 90% or greater, or about 95% or greater.

The specific action of the antimicrobial is highly dependent on its structure. Without being bound by the theory, it is believed that the glucoheptonate moiety of the compounds of the present invention attaches itself to the outer membrane(s) of the virus by hydrogen bonding, potentially allowing for a "Trojan Horse" delivery mechanism of the quaternary ammonium or free base portion. It is further believed that the seven carbon glucoheptonate chain may offer improved efficacy over other polyhydroxycarboxylic chains such as the six carbon gluconate chain.

Glucoheptonate compounds of the present invention may also be useful as algaecides, bactericides, tuberculocides, sporicides, and/or fungicides. The affinity of glucoheptonates for calcium and other polyvalent cations may also enhance the antimicrobial efficacy of the compounds, especially when cell membranes of the target microbe contain calcium or other critical polyvalent ions in the outer layers.

Without being bound to the theory, it is believed that counterions based on polyhydrocarboxylic acids or sugar acids (e.g., glucoheptonates) are useful against Gram-negative and Gram-positive bacterial cells because these counterions have similar structure to elements of the outer membrane of the bacteria cells. Gram-negative microbes have outer structures that are composed of lipopolysaccharides, which are long chain monosaccharide units joined by glycosidic bonds. Gram-positive bacteria are composed of peptidoglycan, which is comprised of alternating polymeric amine sugars. Similarly, enveloped viruses often contain glycoproteins, which contain oligosaccharide chains. It is believed that hydrogen bonding occurs between the oligosaccharide structures and sugar acid counterions, enhancing the destructive effect of the cationic portion of the molecule. It is further believed that the associations between the cell structures and the counterion can lead to "Trojan Horse" mechanisms of cell destruction referenced above.

Although reference is made herein to specific pathogens or microbes that may be reduced or destroyed by the compounds of the present invention, it should be understood that this discussion is not limiting. As explained in Sattar, Syed, *Journal of AOAC International*. Vol. 90, No. 6, 2007, it is generally recognized in the field that there is a hierarchy of susceptibility of viruses to chemical disinfectants. For example, enveloped viruses are generally highly susceptible to chemical disinfectants. It is reasonably expected that a chemical disinfectant determined to be useful for a particular virus will also be useful for viruses having the same or higher levels of susceptibility to chemical disinfectants.

In certain embodiments, the compounds of the present invention (e.g., chlorhexidine diglucoheptonate, benzalkonium glucoheptonate, glucoheptonic acid, etc.) are effective at the reduction or destruction of certain undesirable microbes. The compounds of the present invention may be useful for the destruction of yeast/fungi, viruses, bacteria, etc.

For example, the compounds of the present invention may be useful for the reduction or destruction of one or more yeast/fungi selected from the group consisting of *Aspergillus*

*niger, Candida albicans, Candida tropicalis, Rhodotorula mucilaginosa*, and *Penicillium* species.

The compounds of the present invention may be useful for the reduction or destruction of one or more species selected from the group consisting of Mastadenovirus and Aviadenovirus (i.e. adenovirus), Norovirus (e.g., Norwalk Virus), Betacoronavirus (e.g., Middle East respiratory syndrome-related coronavirus [MERS-COV] and Severe acute respiratory syndrome coronavirus [e.g., SARS-COV-2]), Ebolavirus (e.g., Zaire ebolavirus), Flavivirus (e.g., West Nile virus and Zika virus), Orthohantavirus (i.e. hantavirus), Varicellovirus (e.g., Equid alphaherpesvirus species and Human alphaherpesvirus 3 [i.e. Varicella-zoster virus]), Rhadinovirus (e.g., Equid gammaherpesvirus species and Human gammaherpesvirus 8), Simplexvirus (e.g., Human alphaherpesvirus species), Lymphocryptovirus (e.g., Human gammaherpesvirus 4 [i.e. Epstein-Barr virus]), Cytomegalovirus (e.g., Human betaherpesvirus 5), Roseolovirus (e.g., Human betaherpesvirus species), Rubivirus (e.g., Rubivirus rubella [i.e. rubella]), Orthonairovirus (e.g., Crimean-Congo hemorrhagic fever orthonairovirus), Alphainfluenzavirus (i.e. Influenza A virus), Betainfluenzavirus (i.e. Influenza B virus), Morbillivirus (e.g., Measles morbillivirus and Canine morbillivirus [i.e. Canine distemper virus]), Respirovirus (e.g., Human respirovirus 1 and 3 [i.e. Human parainfluenza virus 1 and 3]), Orthorubulavirus (e.g., Human orthorubulavirus 2 and 4 [i.e. Human parainfluenza virus 2 and 4], Mammalian orthorubulavirus 5 [i.e. Canine parainfluenza virus 5], Mumps orthorubulavirus [i.e. mumps]), Protoparvovirus (e.g., Carnivore protoparvovirus 1 [i.e. canine parvovirus and feline panleukopenia virus]), Enterovirus (e.g., Enterovirus C [i.e. Poliovirus or polio]), Orthopneumovirus (e.g., Human orthopneumovirus [i.e. Human respiratory syncytial virus, hRSV]), Orthopoxvirus (e.g., Variola virus [i.e. smallpox]), Rotavirus (e.g., bovine rotavirus and human rotavirus), Lentivirus (e.g., Human immunodeficiency virus 1 and 2 [i.e. HIV]), Lyssavirus (e.g., Rabies lyssavirus [i.e. rabies]), and combinations thereof.

In addition, the compounds of the present invention may be useful for the reduction or destruction of the various species commonly known as echovirus (e.g., of the genera *Enterovirus, Orthoreovirus*, and *Parechovirus*), as well as hepatitis A-F (e.g., of the genera *Hepatovirus, Orthohepadnavirus, Hepacivirus, Deltavirus, Orthohepevirus*, and *Alphavirus*).

The compounds of the present invention may be useful for the reduction or destruction of one or more bacteria selected from the group consisting of *Acinetobacter baumannii, Bordatella pertussis, Enterobacter aerogenes, Enterobacter cloacae, Enterococcus faecalis* (VRE), *Enterococcus faecium, Bordatella pertussis, Corynebacterium xerosis, Escherichia coli, Klebsiella pneumoniae, Legionella pneumophila, Listeria monocytogenes, Micrococcus luteus Mycobacterium terrae, Propionibacterium acnes, Staphylococcus aureus*, methicillin-resistant *Staphylococcus aureus* (MRSA), *Staphylococcus epidermidis, Streptococcus pneumoniae, Streptococcus pyogenes, Streptococcus sobrinus, Salmonella enterica, Salmonella abony, Pseudomonas aerginosa, Pseudomonas maltophilia*, and combinations thereof.

As detailed in the examples, Bubble Pressure Tensiometry may be used to evaluate compounds of the present invention (i.e. surface active antimicrobials) for performance in microbial testing. Bubble Pressure Tensiometry differs from other equilibrium (thermodynamic) surface tension measurement techniques in that it provides dynamic (kinetic) information, and the impact of time on the rate and magnitude of surface tension reduction can be observed. Both of these are important parameters in any process that involves surfactants and surfaces, and elucidation of such properties may allow for pre-selection of active biocides. Without being bound by the theory, it is believed that the results of a bubble pressure tensiometry test of a compound may be a useful tool for pre-screening of compounds to determine the relative usefulness as a disinfectant Additionally, without being bound by the theory, the structural differences between gluconate, α-glucoheptonate, and β-glucoheptonate counterions are thought to allow for chlorhexidine salts of the β-isomer to interact more effectively with a microbial membrane.

EXAMPLES

Example 1: Preparing α-Glucoheptonic Acid

An experiment was conducted to prepare a solution of α-glucoheptonic acid.

50 g of an acidic ion exchange resin, as a water/resin slurry, was loaded into a flash chromatography column at ambient temperature. 15 g of sodium α-glucoheptonate was dissolved in 50 g water and then loaded into the column. The column was then eluted with water using five passes of 50 mL each. The resulting eluates were combined to form the solution of α-glucoheptonic acid. The solution was a clear, light straw-colored liquid. The pH of the solution was 2.32, and the solution had a solids content of 8.8 wt. %.

Example 2: Preparing α-Glucoheptonic Acid

A further experiment was conducted to prepare a solution of α-glucoheptonic acid.

150 g of sodium α-glucoheptonate was dissolved in 750 g of water in a first container. 500 g of an acidic ion exchange resin was placed in a second container. The acidic ion exchange resins DOWEX MARATHON MSC and LEWATIT MONOPLUS SP 112 H were tested in this experiment. The liquid from the first container was poured into the second container containing the resin, and the slurry was mixed by pouring one container into the other every 20 minutes for one hour or four hours. The slurry was then filtered to remove the ion exchange resin beads and yield a solution of α-glucoheptonic acid. The solution of α-glucoheptonic acid was a clear, light straw-colored liquid. The solution had a pH of approximately 2.30 and an average solids content of 10 wt. %. The results of this experiment are set forth below in Table 1. "65° C. Solids" represents the weight percentage of solids present in the solution of α-glucoheptonic acid, where the % solids is determined by oven drying at 65° C. The sodium value represents the results of residual sodium quantification, evaluated by Inductively Coupled Plasma (ICP) analysis. The data was collected with a Spectro Blue-EOP-TI instrument using a Lowest Calibration Level (LCL) of 0.25 mg/kg.

TABLE 1

| Ion Exchange Resin | Eq. Resin | Rxn Time | 65° C. Solids | Na (mg/kg) |
|---|---|---|---|---|
| DOWEX MARATHON MSC | ~2.2 | 4 hr | 11.24% | 39.9 |
| DOWEX MARATHON MSC | ~2.2 | 4 hr | 11.56% | 46.3 |
| DOWEX MARATHON MSC | 2.2 | 4 hr | 9.23% | 62.8 |
| LEWATIT MONOPLUS SP 112 H | 1.8 | 4 hr | 9.27% | 68.8 |

TABLE 1-continued

| Ion Exchange Resin | Eq. Resin | Rxn Time | 65° C. Solids | Na (mg/kg) |
|---|---|---|---|---|
| DOWEX MARATHON MSC | 2.0 | 1 hr | 9.70% | 71.6 |
| LEWATIT MONOPLUS SP 112 H | 2.0 | 1 hr | 9.43% | 77.6 |

A portion of the α-glucoheptonic acid was dried at 65° C. in a forced air oven on a flat glass plate to generate a brittle white film. NMR and IR spectra analysis were characteristic of a polyhydroxycarboxylic acid compound in its acidic form. The α-glucoheptonic acid content was determined to be >99% of total isomers by HPLC.

The film material was also heated to 850° C. in a muffle furnace to determine the ash content. The ash content was determined to be 1000 ppm.

Example 3: Preparing β73-Glucoheptonic Acid

An experiment was conducted to prepare a solution of β73-glucoheptonic acid.

50 g of an acidic ion exchange resin, as a water/resin slurry, was loaded into a flash chromatography column at ambient temperature. 33.63 g of a sodium β73-glucoheptonate solution was loaded into the column. The column was then eluted with water and 161 g of a β73-glucoheptonic acid solution was collected. The β73-glucoheptonic acid solution was a clear, dark straw-colored liquid.

Example 4: Preparing β73-Glucoheptonic Acid

A further experiment was conducted to prepare a solution of β73-glucoheptonic acid.

336.3 g of a sodium β73-glucoheptonate solution was dissolved in 564 g of water in a first container. 500 g of an acidic ion exchange resin was placed in a second container. The liquid from the first container was poured into the second container containing the resin, and the slurry was mixed by pouring one container into the other every 20 minutes for four hours. The slurry was then filtered to remove the beads and yield a solution of solution of β73-glucoheptonic acid. The solution of β73-glucoheptonic acid was a clear, dark straw-colored liquid. The solution had a pH of approximately 2.56 and a solids content of approximately 11.4 wt. %. The results of this experiment are set forth below in Table 2. "65° C. Solids" represents the weight percentage of solids present in the solution of β73-glucoheptonic acid, where the % solids is determined by oven drying at 65° C. The sodium value represents the results of residual sodium quantification, evaluated by Inductively Coupled Plasma (ICP) analysis. The data was collected with a Spectro Blue-EOP-TI instrument using a Lowest Calibration Level (LCL) of 0.25 mg/kg.

TABLE 2

| Ion Exchange Resin | Eq. Resin | Rxn Time | 65° C. Solids | Na (mg/kg) |
|---|---|---|---|---|
| DOWEX MARATHON MSC | ~2.2 | 4 hr | 11.41% | 82.9 |
| DOWEX MARATHON MSC | ~2.2 | 4 hr | 11.55% | 83.0 |
| DOWEX MARATHON MSC | ~2.2 | 4 hr | 11.26% | 96.9 |

A portion of the β73-glucoheptonic acid was dried at 65° C. in a forced air oven on a flat glass plate to generate a brittle white film. NMR and IR spectra analysis were characteristic of a polyhydroxycarboxylic acid compound in its acidic form. The ratio of β-glucoheptonic acid to α-glucoheptonic acid was determined to be 2.73 by HPLC (73.2% β isomer). The film material was heated to 850° C. in a muffle furnace to determine the ash content. This procedure yielded no recoverable ash.

Example 5: Preparing β81-Glucoheptonic Acid

An experiment was conducted to prepare a solution of β81-glucoheptonic acid.

476 g of a liquid comprising sodium glucoheptonate having a β-isomer content of 81% (referred to herein as sodium β81-glucoheptonate) was added to a container and mixed with 120 mL of methanol. In certain embodiments, the sodium β81-glucoheptonate may be prepared in the manner set forth in U.S. Pat. No. 3,084,188. The container was placed in a refrigerator (2-8° C. and allowed to rest overnight. 20% of the volume of the container comprised crystals after resting overnight. The supernatant was dried at 65° C. in a forced air oven on a flat glass plate for a period of two days and generated a solid. 10.57 g of the solid was removed from the glass plate, dissolved in 54 g of water, and combined with 36.3 g of an acidic ion exchange resin. The slurry was stirred every 20 minutes for a period of four hours. At the conclusion of this time period, the slurry was filtered to remove the ion exchange resin. The resulting solution of β81-glucoheptonic acid was a clear, dark straw-colored liquid with a pH of 1.93 and a solids content of 11.0 wt. %.

Example 6: Preparing Benzalkonium α-Glucoheptonate

An experiment was conducted to prepare benzalkonium α-glucoheptonate.

1000 g of benzalkonium chloride was added to a round bottom flask equipped with overhead stirrer assembly. 545 g of sodium α-glucoheptonate was then added to the flask and the flask was mixed for 45 minutes. The temperature was increased from 30° C. to 90° C. and maintained at about 90° C. for approximately 40 hours. During the final 20 hours, a slow nitrogen purge was maintained to remove excess moisture. The target moisture content was less than 1%. The result of this reaction was a brown paste having a pH of 6.5 (5% aq.). The theoretical yield was determined to be >99% benzalkonium α-glucoheptonate.

Titration with silver nitrate was undertaken and it was determined that the resulting material comprised 10.6 wt % sodium chloride.

Example 7: Testing Glucoheptonate Salts

Solutions of chlorhexidine di-α-glucoheptonate (RM13), chlorhexidine di-β73-glucoheptonate (RM14), and chlorhexidine di-β81-glucoheptonate (RM15) were prepared for further testing. Chlorhexidine digluconate (RM12) was also prepared.

For each solution, chlorhexidine was slurried with water, the respective acid (gluconic acid, α-glucoheptonic acid, β73-glucoheptonic acid, or β81-glucoheptonic acid) was mixed until dissolved, and the mixture was diluted with water. The resulting solutions were 0.10 molar solutions with respect to the chlorhexidine concentration. Molar ratios of the glucoheptonic or gluconic acid to chlorhexidine varied from 2.0:1 to 2.6:1.

Multiple solutions were prepared utilizing differing molar ratios of the chlorhexidine and the respective acid (gluconic acid, α-glucoheptonic acid, Bβ73-glucoheptonic acid, or β81-glucoheptonic acid). Table 3 below sets forth the theoretical masses required for preparing a 0.10 M salt solution based on the noted molar ratio.

TABLE 3

| Solution No. | Chlor-hexidine (g) | Corres-ponding Acid (g) | Molar Ratio of Acid:Chlorhexidine | Product Salt |
|---|---|---|---|---|
| RM12A | 5.05 | 3.93 | 2.0:1 | Chlorhexidine |
| RM12B | 5.05 | 4.51 | 2.3:1 | digluconate |
| RM12C | 5.05 | 5.10 | 2.6:1 | (RM12) |
| RM13A | 5.05 | 4.52 | 2.0:1 | Chlorhexidine |
| RM13B | 5.05 | 5.20 | 2.3:1 | di-α- |
| RM13C | 5.05 | 5.88 | 2.6:1 | glucoheptonate (RM13) |
| RM14A | 5.05 | 4.52 | 2.0:1 | Chlorhexidine |
| RM14B | 5.05 | 5.20 | 2.3:1 | di-β73- |
| RM14C | 5.05 | 5.88 | 2.6:1 | glucoheptonate (RM14) |
| RM15A | 5.05 | 4.52 | 2.0:1 | Chlorhexidine |
| RM15B | 5.05 | 5.20 | 2.3:1 | di-β81- |
| RM15C | 5.05 | 5.88 | 2.6:1 | glucoheptonate (RM15) |

Example 8: Bubble Tensionmetry

Dynamic surface tensions of certain formulations were measured using a KRÜSS BP100 BPT Mobile bubble pressure tensiometer. Samples of the solution of Example 7 were tested by adding the test solution to a glass dish and lowering the disposable capillary tip and temperature probe into the solution. The dynamic setting was selected, and the instrument was set to collect 30 data points, the bubble age increasing from about 10 ms to about 30,000 ms.

Bubble tensiometry was used to calculate the Critical Micelle Concentration (CMC) value for each of the solutions. The results are set forth below in Table 4.

TABLE 4

| Salt | Calculated CMC (M) |
|---|---|
| RM12A | 0.0168 |
| RM12B | 0.0195 |
| RM12C | 0.0195 |
| RM13A | 0.0200 |
| RM13B | 0.0167 |
| RM13C | 0.0198 |
| RM14A | 0.0168 |
| RM14B | 0.0167 |
| RM14C | 0.0166 |
| RM15A | 0.0173 |

Each of solutions RM12A, RM13A, RM14A-RM14C, and RM15A were tested using the above procedures and are presented in FIGS. 1-7.

Figure 2:
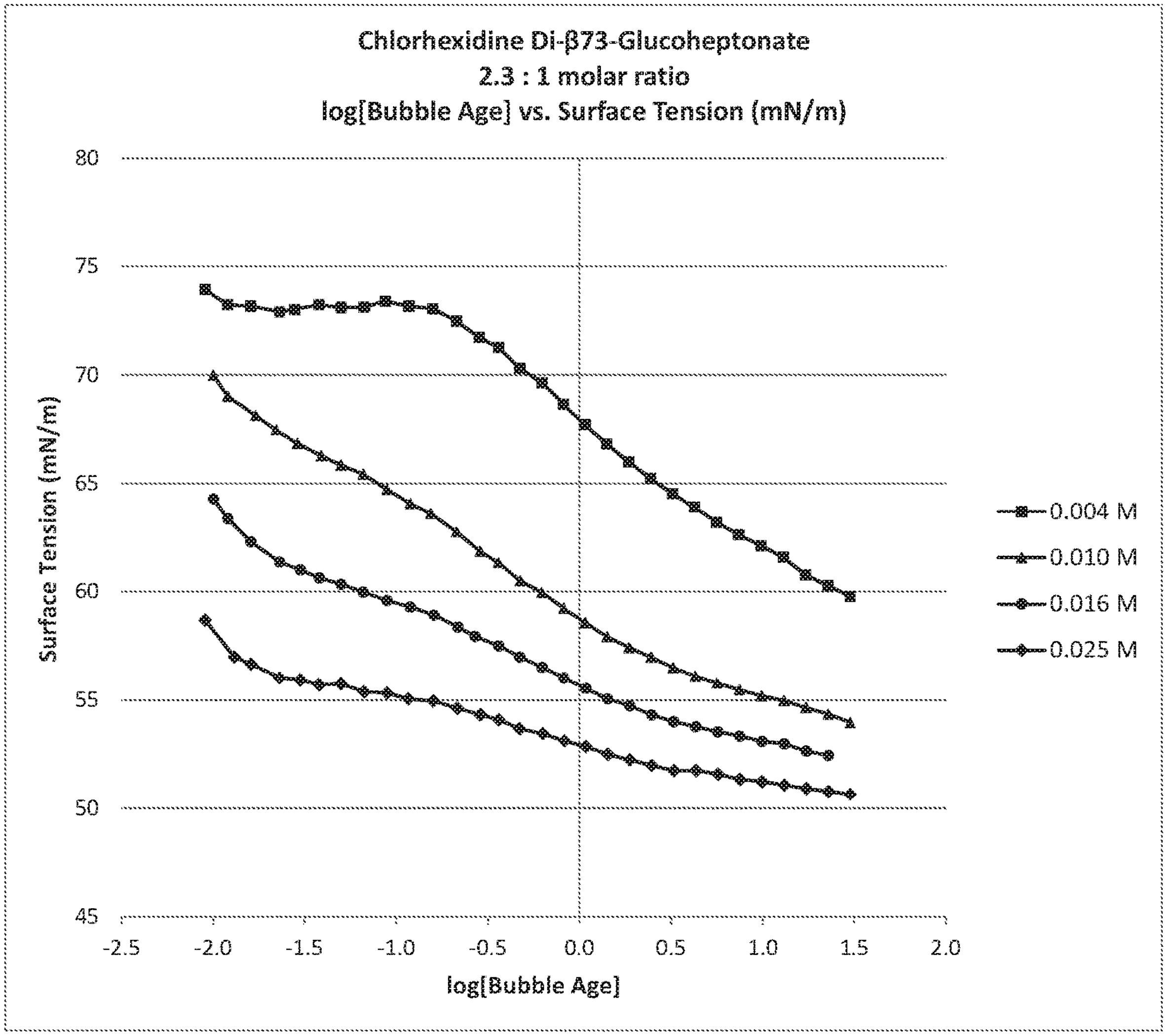
FIG. 2 presents a comparison of the bubble age to surface tension for RM14B at various concentrations.
Figure 3:
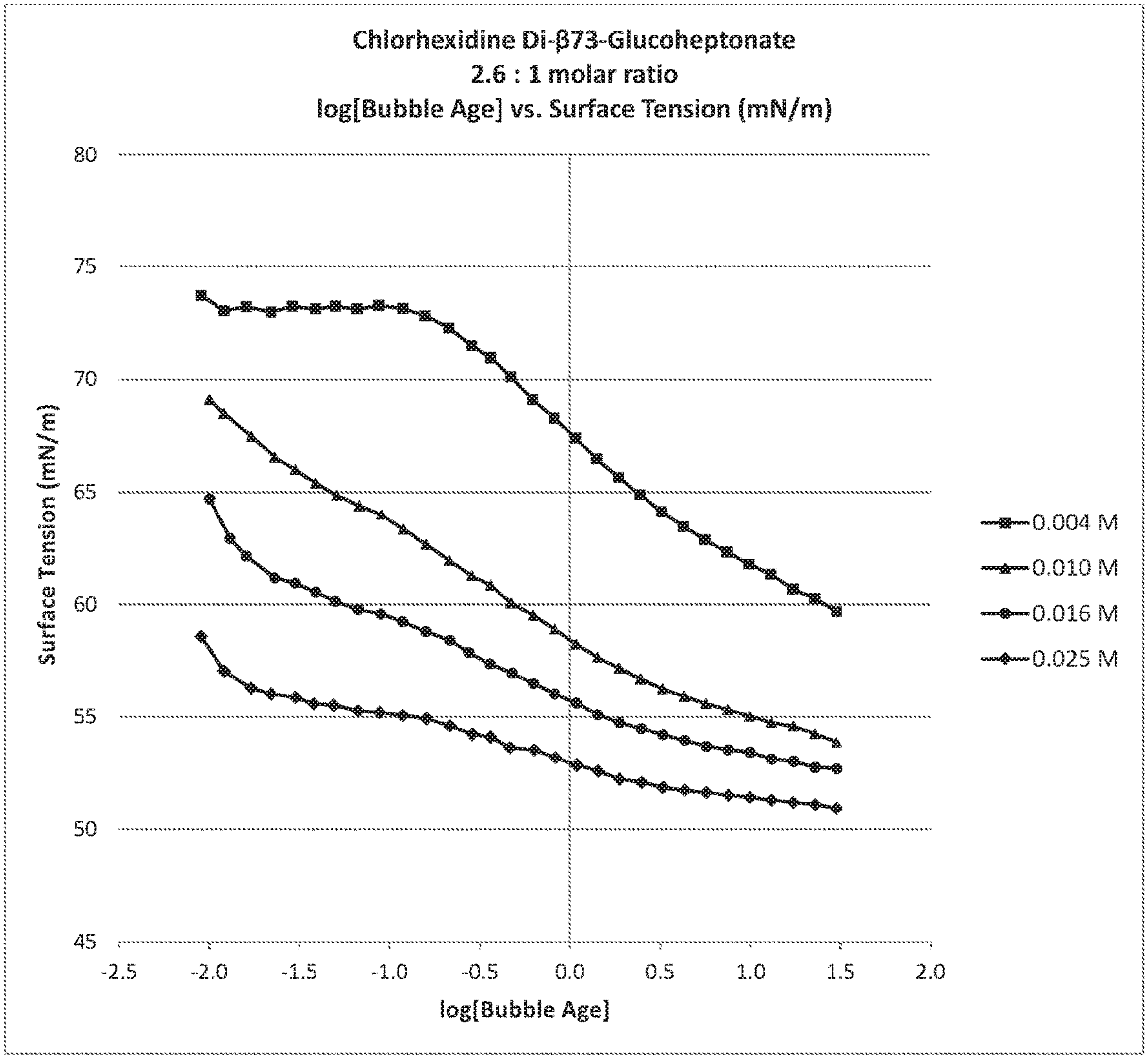
FIG. 3 presents a comparison of the bubble age to surface tension for RM14C at various concentrations.
Figure 4:
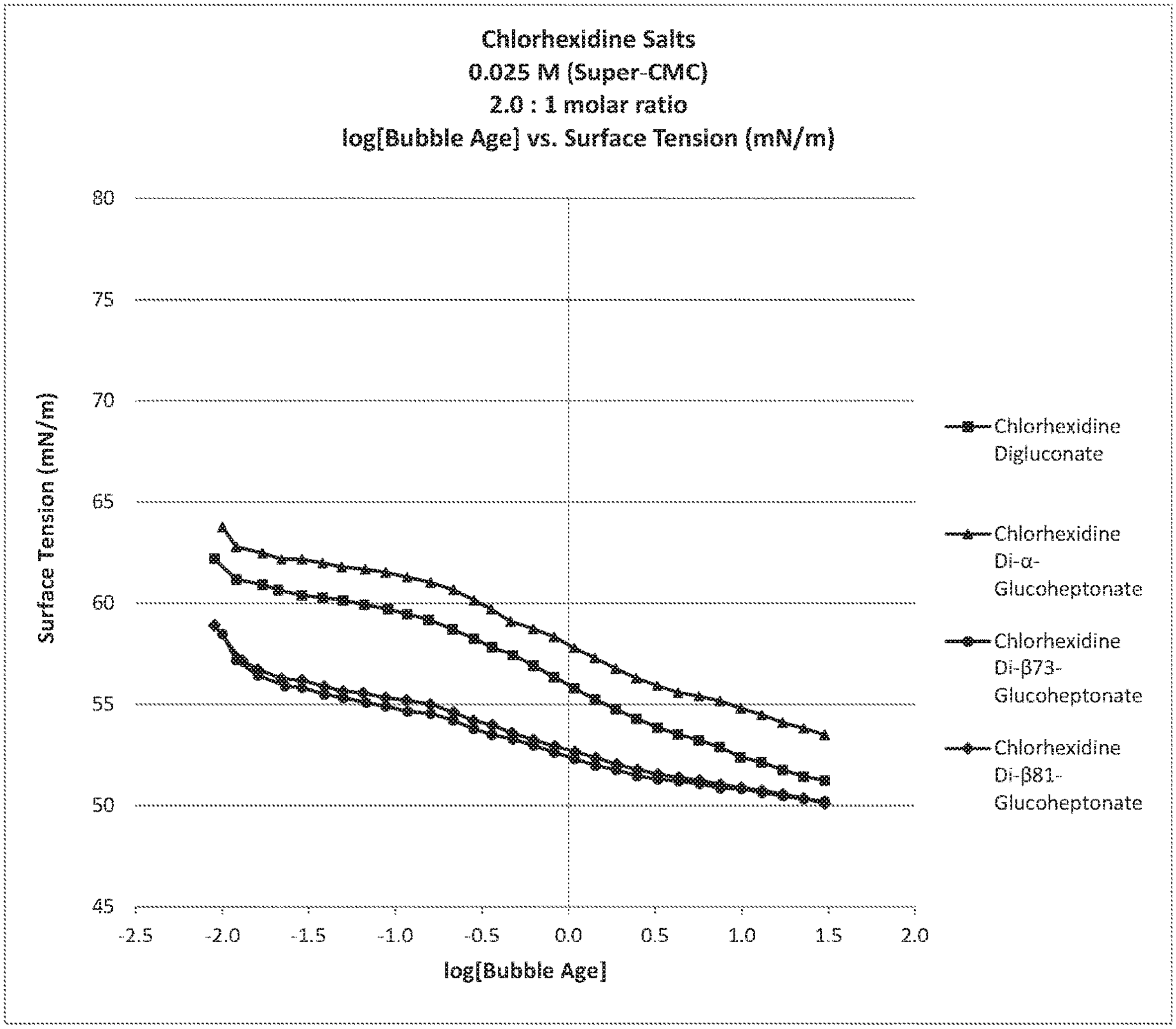
FIG. 4 presents a comparison of the bubble age to surface tension for RM12A, RM13A, RM14A, and RM15A at super-CMC concentrations.
Figure 5:
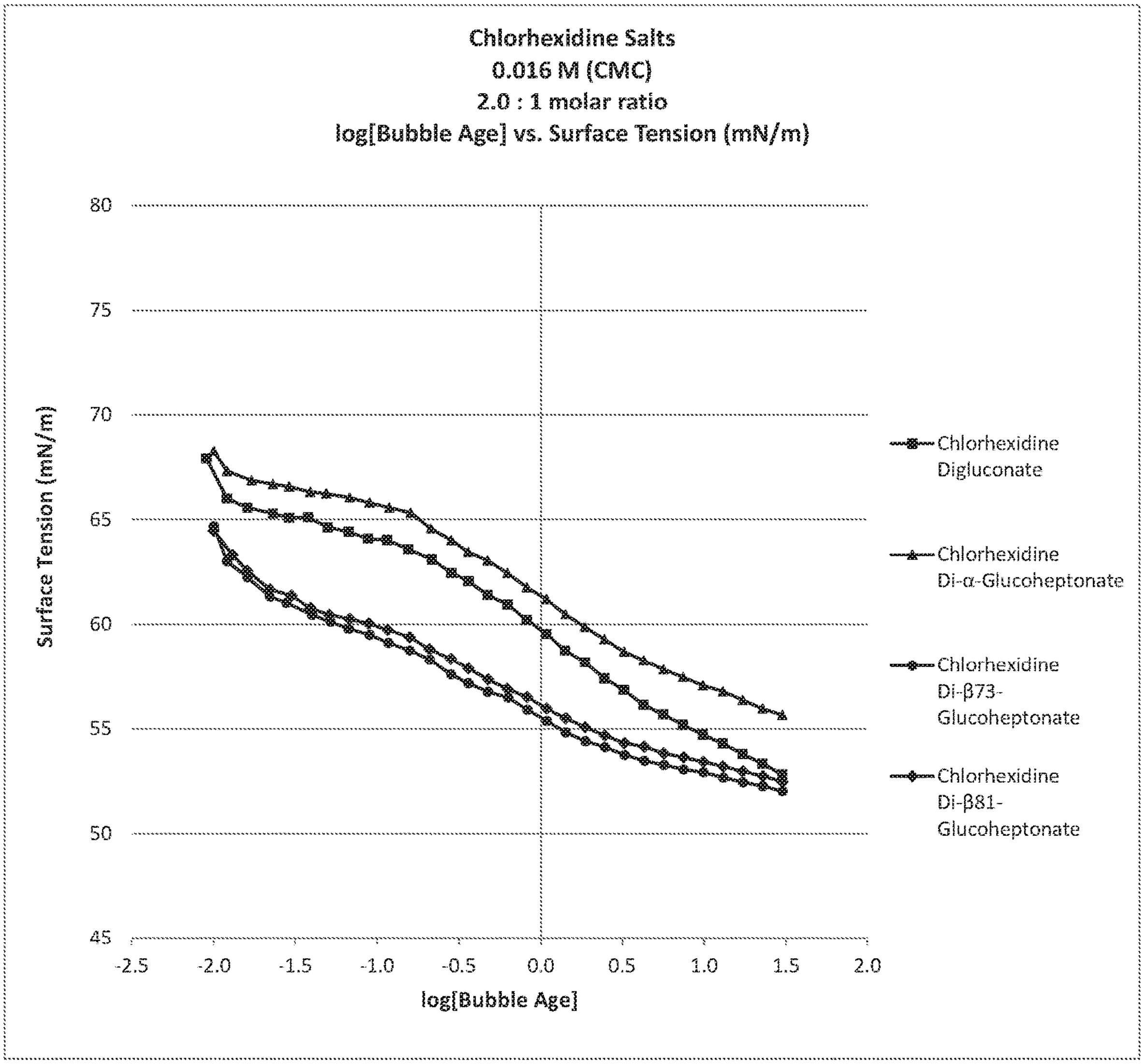
FIG. 5 presents a comparison of the bubble age to surface tension for RM12A, RM13A, RM14A, and RM15A at CMC concentrations.
Figure 6:
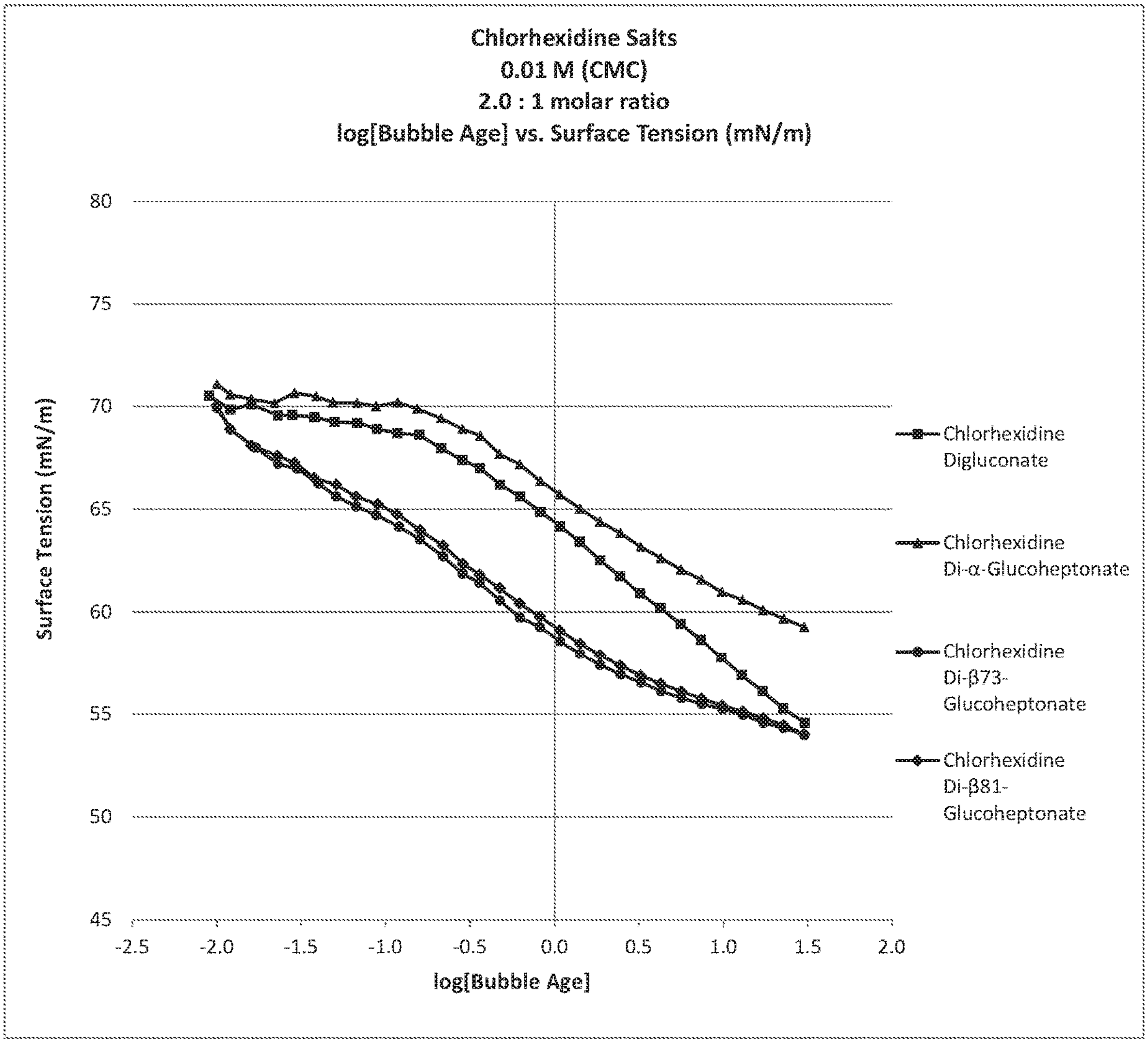
FIG. 6 presents a comparison of the bubble age to surface tension for RM12A, RM13A, RM14A, and RM15A at CMC concentrations.
Figure 7:
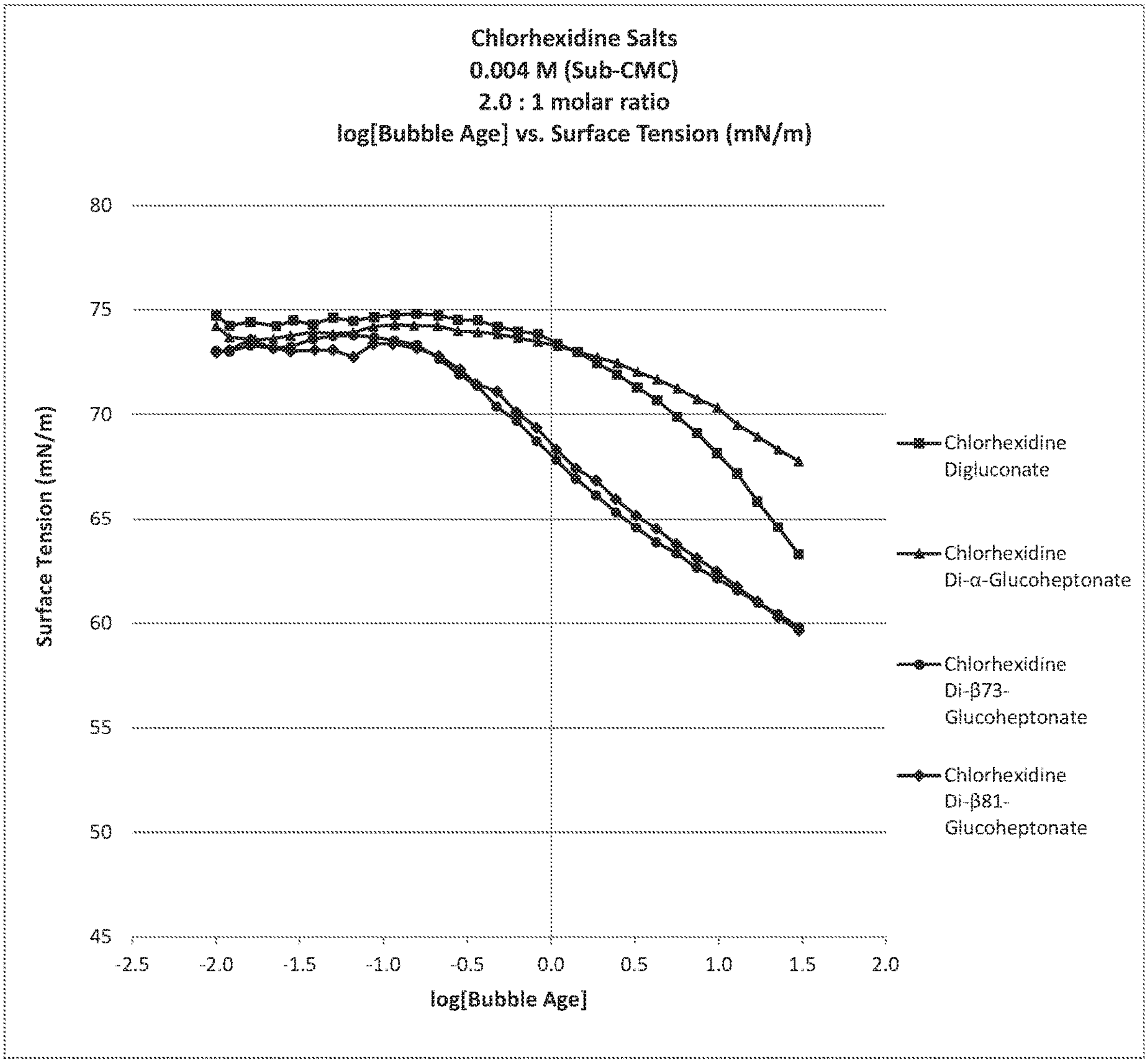
FIG. 7 presents a comparison of bubble age to surface tension for RM12A, RM13A, RM14A, and RM15A at sub-CMC concentrations.

FIG. 1 presents a comparison of the bubble age to surface tension for RM14A at CMC, sub-CMC, and super-CMC concentrations. FIG. 2 presents a comparison of the bubble age to surface tension for RM14B at CMC, sub-CMC, and super-CMC concentrations. FIG. 3 presents a comparison of the bubble age to surface tension for RM14C at CMC, sub-CMC, and super-CMC concentrations. FIG. 4 presents a comparison of the bubble age to surface tension for RM12A, RM13A, RM14A, and RM15A at super-CMC concentrations. FIG. 5 presents a comparison of the bubble age to surface tension for RM12A, RM13A, RM14A, and RM15A at CMC concentrations. FIG. 6 presents a comparison of the bubble age to surface tension for RM12A, RM13A, RM14A, and RM15A at CMC concentrations. FIG. 7 presents a comparison of bubble age to surface tension for RM12A, RM13A, RM14A, and RM15A at sub-CMC concentrations.

It is notable that chlorhexidine di-β73-glucoheptonate and chlorhexidine di-β81-glucoheptonate salts appeared to cause surface tension to fall more rapidly and to a lower value than either the di-α-glucoheptonate or the comparative digluconate salt. This was an unexpected finding, and appears to indicate that the chlorhexidine di-β-glucoheptonate salts associate in such a manner that allows for a greater reduction in surface tension. Without being bound to the theory, it is believed that there is an improvement in molecular-level kinetics or the electrostatic process, which allows for a faster reduction in the surface tension and generally a lower surface tension value.

The data further indicate that chlorhexidine di-β73-glucoheptonate and di-β81-glucoheptonate salts behave similarly. To achieve the desired results, it is believed that a β-isomer concentration of at least about 25% should be used. In one embodiment, the composition comprises 25% β-isomer, 75% α-isomer.

As demonstrated by the results discussed herein, it also appears that antimicrobial behavior favors chlorhexidine diglucoheptonate salts prepared with β-isomers, and that biocidal activity exceeds the performance of the comparative standard, digluconate salts. Therefore, without being bound by the theory it is believed that dynamic surface tension may be a useful tool for pre-screening of compounds that are capable of reducing surface tension, at either sub-CMC, CMC, or super-CMC concentrations, and ultimately, in determining the usefulness of a compound as a disinfectant.

Example 9: Conductivity Testing

Conductivities were measured using a VWR 23609-216 Pure $H_2O$ Tester conductivity meter. The meter probe was submerged into the test solution and swirled gently. Once the meter settled, the value was recorded.

The conductivity of the solutions of Example 7 were tested at dilutions ranging from 0.1 M to 0.001 M. The data was plotted on a logarithmic scale and analyzed in the style of Heard and Ashworth. For each sample, three graphs were reported and fitted with a trend curve: outer data points, inner data points, all data points. This data was used as set forth below to calculate the Critical Micelle Concentration (CMC). An average CMC value was determined from the three trend samples (outer data points, inner data points, all data points) in order to more accuracy predict the CMC value.

Figure 8:
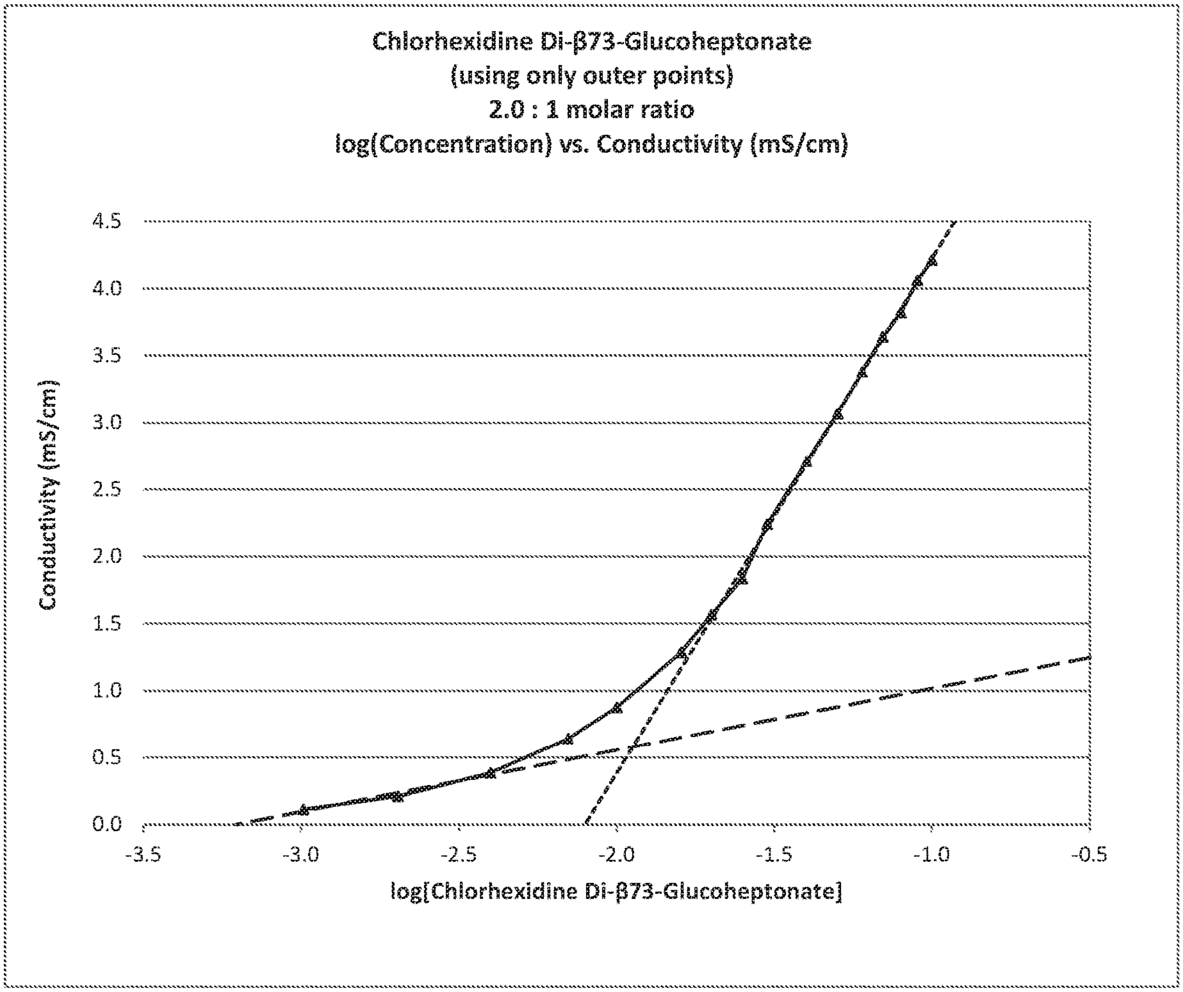
FIG. 8 reports the conductivity for RM14A for the outer data points.
Figure 9:
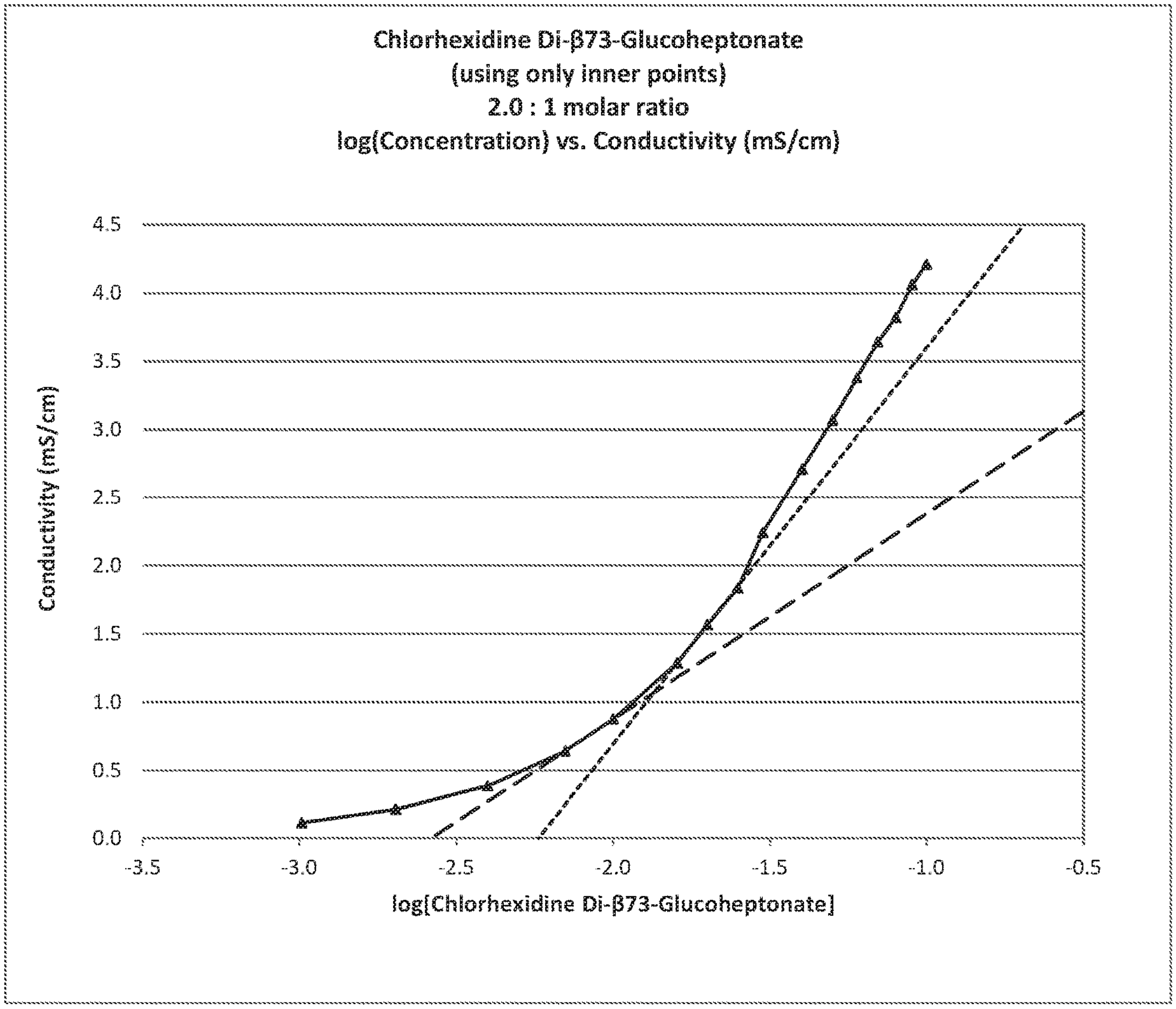
FIG. 9 reports the conductivity for RM14A for the inner data points.
Figure 10:
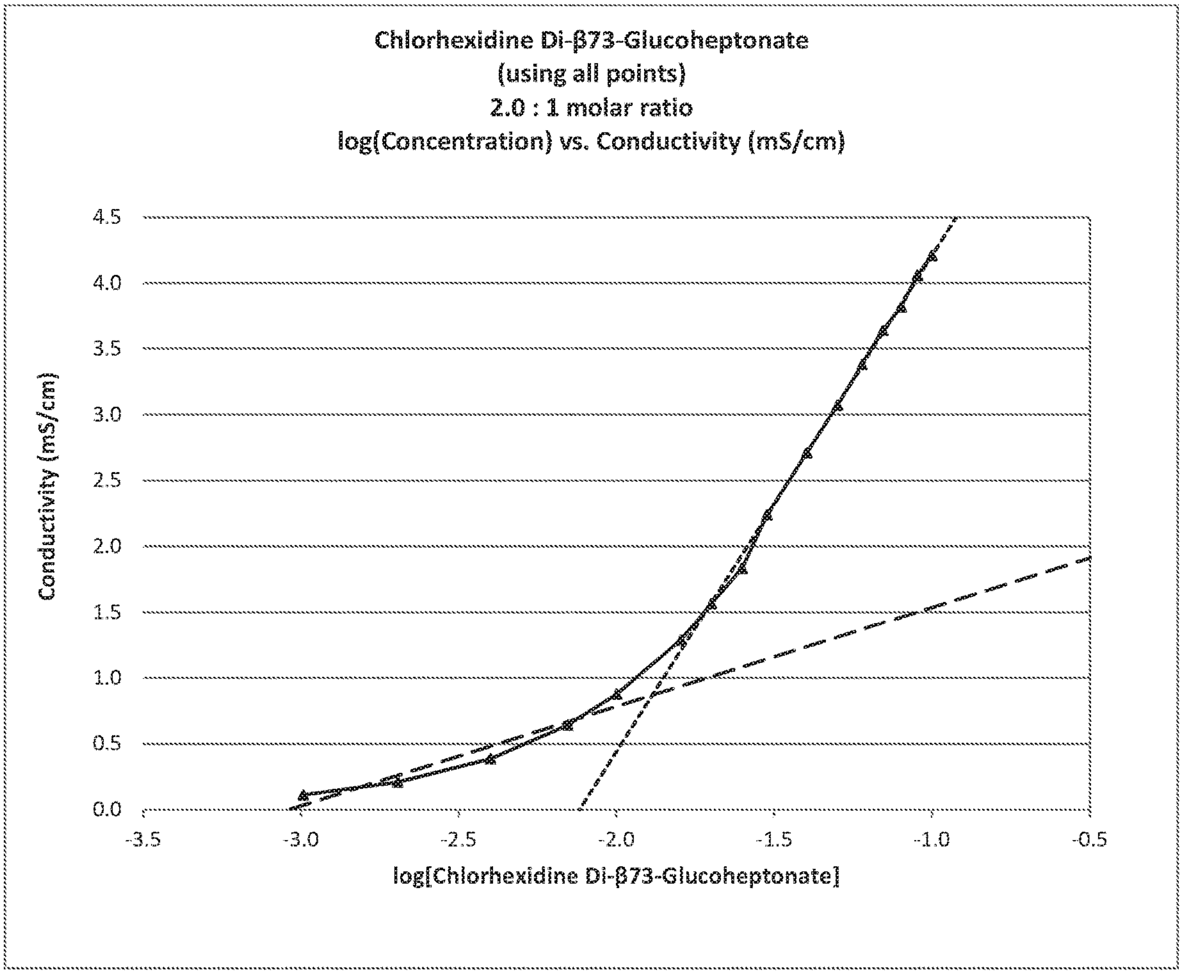
FIG. 10 reports the conductivity for RM14A for the all data points.

FIGS. 8-10 reports the conductivity for RM14A as the outer data points, inner data points, and all data points, respectively.

LINEST was utilized to determine the slope and intercept for each line, and a combination of INTERCEPT and SLOPE was used to determine the intersection of the two fitted lines. The Critical Micelle Concentration (CMC) was determined for each of these plots by the intercept of the two lines. Set forth below in Table 5 is the calculated CMC for each graph and the average CMC.

TABLE 5

| | Calculated CMC (M) | | | |
|---|---|---|---|---|
| Solution No. | Outer Points | Inner Points | All Points | Average |
| RM12A | 0.0118 | 0.0128 | 0.0133 | 0.0126 |
| RM12B | 0.0117 | 0.0131 | 0.0133 | 0.0127 |
| RM12C | 0.0116 | 0.0143 | 0.0133 | 0.0131 |
| RM13A | 0.0115 | 0.0122 | 0.0132 | 0.0123 |
| RM13B | 0.0116 | 0.0131 | 0.0132 | 0.0126 |
| RM13C | 0.0113 | 0.0134 | 0.0130 | 0.0126 |
| RM14A | 0.0113 | 0.0135 | 0.0130 | 0.0126 |
| RM14B | 0.0113 | 0.0152 | 0.0132 | 0.0132 |
| RM14C | 0.0111 | 0.0156 | 0.0131 | 0.0133 |
| RM15A | 0.0113 | 0.0154 | 0.0133 | 0.0133 |

Example 10: Refractive Index Analysis

Refractive indices were measured using a Mettler Toledo RM40 LiquiPhysics Excellence temperature-controlled refractometer. The prism was covered by several drops of test solution and the cover lowered. The refractive indices were collected at 25° C.

Figure 11:
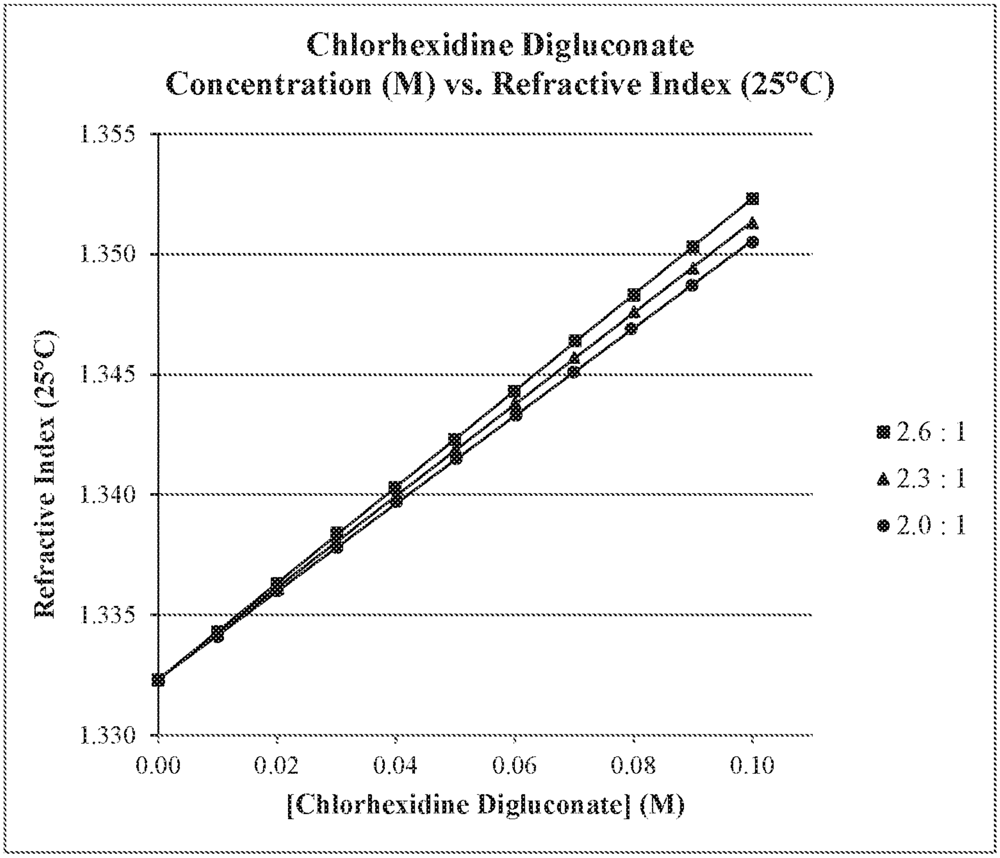
FIG. 11 reports the refractive index of RM12A, RM12B and RM12C.
Figure 12:
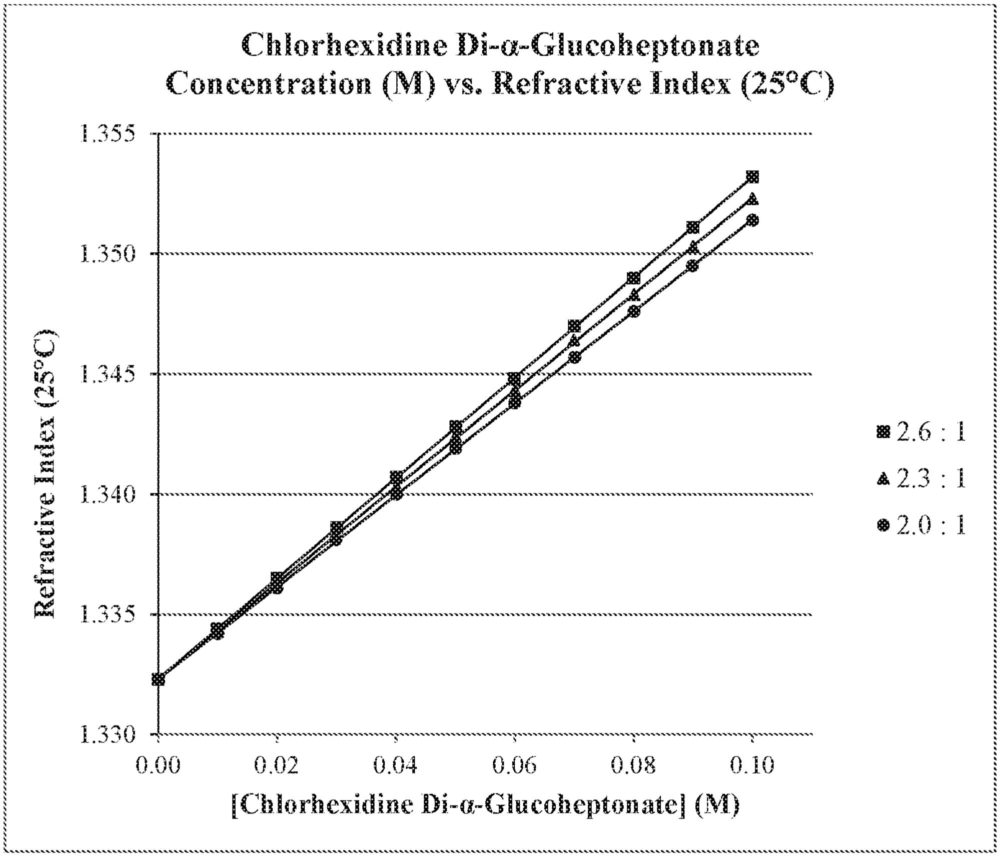
FIG. 12 reports the refractive index of RM13A, RM13B and RM13C.
Figure 13:
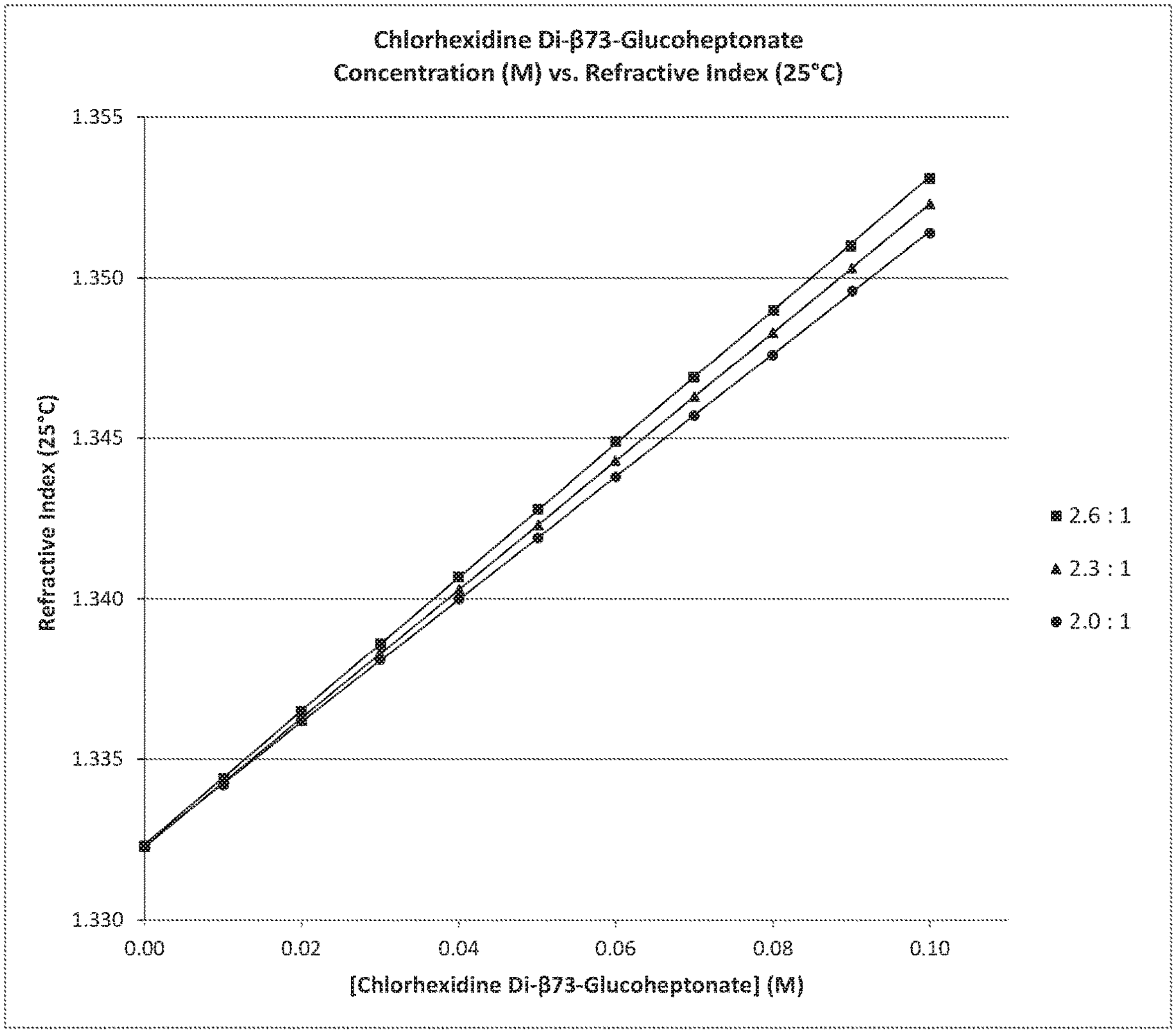
FIG. 13 reports the refractive index of RM14A, RM14B and RM14C.
Figure 14:
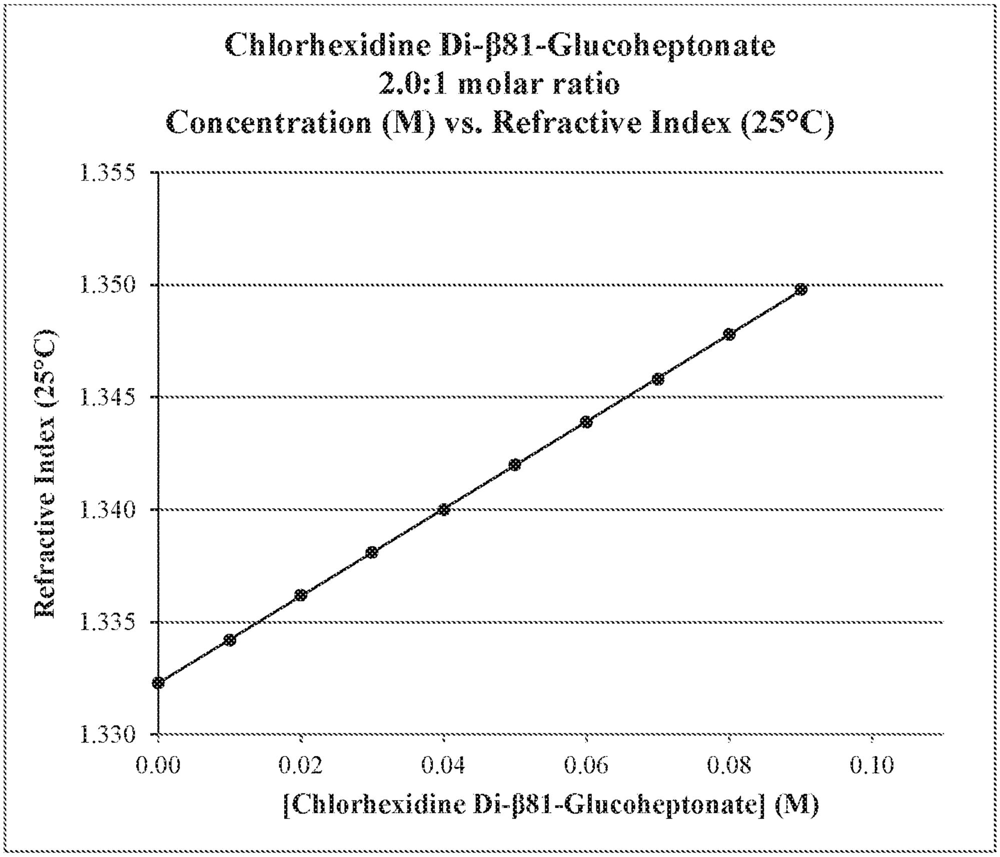
FIG. 14 reports the refractive index of RM15A.

Decreasing molar concentrations of each sample (i.e. 0.10 M, 0.08 M, 0.06 M, etc.) were tested to determine the refractive index of the respective sample. RM12A, RM12B, and RM12C are reported in FIG. 11. RM13A, RM13B, and RM13C are reported in FIG. 12. RM14A (reported as 2.0:1), RM14B (reported as 2.3:1), and RM14C (reported as 2.6:1) are shown in FIG. 13. RM15A is reported in FIG. 14.

Example 11: NMR Analysis

In a further experiment, the concentration of α-glucoheptonic acid and β73-glucoheptonic acid in the aqueous solutions of Example 2 and 4, respectively, was evaluated by NMR analysis. Each respective aqueous solution was combined with an approximately equal mass of deuterium oxide. An excess of sodium hydroxide (45% aqueous solution) was added and then approximately 0.17 equivalents of sodium acetate was added to the solution to form a mixture. The mixture was stirred until completely homogeneous, and subjected to NMR analysis. NMR data was collected using a BRUKER Avance-III 400 MHz.

Characteristic peaks in the $^{1}$H-NMR spectra for glucoheptonate and acetate were identified and integrated. The integrations were converted to moles using the nominal integral for each peak, and then compared in order to calculate the molar ratio of glucoheptonate to acetate. This ratio was then used to calculate the starting concentration of glucoheptonic acid in solution. A comparison of weight percentage of solids (measured at 65° C.) and % activity (via 1H-NMR) for select samples is set forth below in Table 6.

TABLE 6

| Sample | Compound | Wt. % Solids (at 65° C.) | % Activity ($^{1}$H-NMR) |
|---|---|---|---|
| Solution of Example 2 | α-Glucoheptonic Acid | 11.24%<br>9.70% | 10.33%<br>8.59% |
| Solution of Example 4 | β73-Glucoheptonic Acid | 11.41% | 9.32% |

Example 12: NMR Analysis

In a further experiment, RM13A and RM14A of Example 7 were subjected to NMR analysis. RM13A or RM14A were pipetted onto separate glass dishes and allowed to dry overnight in a 65° C. forced air oven. A small magnetic stirbar and deuterium oxide were then added to each dish. The mixture was stirred until completely homogeneous, and subjected to NMR analysis. NMR data was collected using a BRUKER Avance-II 300 MHz.

NMR analysis was also used to determine the glucoheptonate to chlorhexidine molar ratio in RM13A and RM14A. Aqueous samples of RM13A and RM14A were diluted to approximately 10% in deuterium oxide and subjected to NMR analysis. NMR data was collected using a BRUKER Avance-II 300 MHz. Characteristic peaks in the $^{1}$H-NMR spectra for chlorhexidine and glucoheptonate were identified and integrated. The integrations were converted to moles using the nominal integral for each peak, and then compared in order to calculate the molar ratio of glucoheptonate to chlorhexidine.

Example 13: Antimicrobial Testing—Chlorhexidine Salts

Select compounds were tested for antimicrobial activity using ASTM method E2315-16 (Standard Guide for Assessment of Antimicrobial Activity using a Time-Kill Procedure). Six microbes were tested: *Candida albicans, Staphylococcus aureus, Staphylococcus epidermidis. Escherichia coli, Salmonella abony*, and *Listeria monocytogenes.*

Four chlorhexidine salts were tested: chlorhexidine di-α-glucoheptonate (Sample G), chlorhexidine di-β73-glucoheptonate (Sample H), chlorhexidine digluconate (Sample I), and chlorhexidine diacetate (Sample P). Both chlorhexidine diglucoheptonate salts were prepared at a 2:1 molar ratio of glucoheptonic acid to chlorhexidine. Dilutions of each salt were prepared using sterile water (20-30 ppm hardness), to achieve the desired wt. % concentration.

Table 7 sets forth the Log Reduction data at 30 seconds for varying concentrations of each sample.

TABLE 7

| | Sample G | | | Sample H | | | Sample I | | | Sample P | | |
|---|---|---|---|---|---|---|---|---|---|---|---|---|
| Microbe | 0.20% | 0.60% | 1.00% | 0.20% | 0.60% | 1.00% | 0.20% | 0.60% | 1.00% | 0.20% | 0.60% | 1.00% |
| *Candida albicans* | 0.75 | 1.45 | 4.56 | 4.26 | 4.56 | 4.51 | 2.91 | 4.35 | 6.40 | 2.56 | 3.35 | 4.48 |
| *Staphylococcus areus* | 0.77 | 1.07 | 3.06 | 0.76 | 3.19 | 4.33 | 1.77 | 3.07 | 3.37 | 3.22 | 4.93 | 5.07 |
| *Staphylococcus epidermidis* | 0.95 | 1.91 | 3.65 | 1.47 | 2.65 | 3.75 | 2.00 | 3.08 | 3.25 | 1.57 | 3.57 | 3.75 |
| *Escherichia coli* | 3.57 | 3.66 | 3.77 | 2.39 | 2.87 | 3.77 | 2.93 | 3.07 | 3.27 | 1.54 | 1.59 | 3.07 |
| *Salmonella abony* | 3.04 | 3.14 | 3.39 | 3.14 | 3.26 | 3.44 | 1.86 | 2.63 | 2.89 | 2.17 | 3.34 | 4.34 |
| *Listeria monocytogenes* | 1.34 | 1.49 | 4.99 | 1.57 | 4.99 | 5.27 | 1.99 | 3.13 | 3.91 | 1.29 | 1.36 | 1.55 |

TABLE 7-continued

| Microbe | Sample G 0.20% | Sample G 0.60% | Sample G 1.00% | Sample H 0.20% | Sample H 0.60% | Sample H 1.00% | Sample I 0.20% | Sample I 0.60% | Sample I 1.00% | Sample P 0.20% | Sample P 0.60% | Sample P 1.00% |
|---|---|---|---|---|---|---|---|---|---|---|---|---|
| Average, all microbes | 1.74 | 2.12 | 3.90 | 2.27 | 3.59 | 4.18 | 2.24 | 3.22 | 3.85 | 2.06 | 3.02 | 3.71 |
| Std. Dev. | 1.14 | 0.95 | 0.67 | 1.16 | 0.87 | 0.61 | 0.48 | 0.53 | 1.18 | 0.67 | 1.22 | 1.15 |

As illustrated in this table, numerous tests exceeded the >99.9% kill standard at 30 seconds by exhibiting a Log Reduction of at least about 3. EPA methodologies generally consider a product to be a sanitizer when there is a Log 3 Reduction in the microbial population at five minutes, using ASTM test method E1153.

Both glucoheptonate salts demonstrated efficacy in the ASTM E2315-16 Time-Kill Test. However, at lower concentrations, the di-β73-glucoheptonate salt demonstrated better performance than the di-α-glucoheptonate salt.

The di-α-glucoheptonate salt performed very strongly against *Candida albicans* and *Listeria monocytogenes*, and, like the di-β73-glucoheptonate salt, outperformed both chlorhexidine digluconate and diacetate. The dramatic increase in performance may be related to aggregation phenomena that are known to take place with chlorhexidine salts at increasing concentrations.

Samples G, H, I, and P were also tested at a concentration of 0.60 wt % active and evaluated for the average Log Reduction in microbial population at 10 minutes, across all microbes. The results are set forth below in Table 8.

TABLE 8

| | Sample | | | |
|---|---|---|---|---|
| | G | H | I | P |
| Log Reduction (LR) | 3.85 | 5.25 | 4.84 | 4.09 |

A further test was conducted at a concentration of 1.0 wt % active and evaluated for the average Log Reduction in microbial population at 10 minutes, across all microbes. The results are set forth below in Table 9.

TABLE 9

| | Sample | | | |
|---|---|---|---|---|
| | G | H | I | P |
| Log Reduction (LR) | 5.34 | 5.51 | 5.46 | 5.17 |

Example 14: Antimicrobial Testing—Glucoheptonic Acids

Two glucoheptonic acids were evaluated for antimicrobial activity against the same six microbes as Example 13. Sample L was α-glucoheptonic acid. Sample M was β73-glucoheptonic acid. The results are set forth below.

TABLE 10

Sample L (α-glucoheptonic acid)

| Concentration, % w/w | Microbe | Contact Time | Log Reduction (LR) |
|---|---|---|---|
| 2.5 | *C. albicans* | 10 minutes | 3.65 |
| 5.0 | *C. albicans* | 10 minutes | 3.00 |
| 2.5 | *S. epidermidis* | 10 minutes | 3.39 |
| 5.0 | *S. epidermidis* | 5 minutes | 3.05 |
| 5.0 | *S. epidermidis* | 10 minutes | 3.50 |

TABLE 11

Sample M (β73-glucoheptonic acid)

| Concentration, % w/w | Microbe | Contact Time | Log Reduction (LR) |
|---|---|---|---|
| 5.0 | *C. albicans* | 5 minutes | 3.47 |
| 5.0 | *C. albicans* | 10 minutes | 4.00 |
| 2.5 | *S. aureus* | 10 minutes | 3.13 |
| 5.0 | *S. aureus* | 5 minutes | 4.07 |
| 5.0 | *S. aureus* | 10 minutes | 4.13 |
| 1.0 | *S. epidermidis* | 10 minutes | 3.47 |
| 2.5 | *S. epidermidis* | 5 minutes | 3.17 |
| 2.5 | *S. epidermidis* | 10 minutes | 3.50 |
| 5.0 | *S. epidermidis* | 5 minutes | 3.39 |
| 5.0 | *S. epidermidis* | 10 minutes | 3.47 |

Example 15: Antimicrobial Testing—Benzalkonium Salts

Benzalkonium salts were also tested using the same procedure as set forth in Example 13. The samples were benzalkonium chloride ($C_{12}$-$C_{16}$) (Sample C), benzalkonium chloride ($C_{12}$-$C_{14}$) (Sample D), benzalkonium chloride in combination with a stoichiometric amount of α-glucoheptonate (Sample F), and benzalkonium chloride in combination with a molar excess of α-glucoheptonate (Sample N). Sample F was prepared by mixing and extensively heating a stoichiometric quantity (1:1) of sodium α-glucoheptonate with benzalkonium chloride, typified by the $C_{12-14}$ alkyl chain. Sample N was prepared by simply blending benzalkonium chloride, typified by the $C_{12-16}$ chain, with a molar excess of sodium α-glucoheptonate (1.6:1). Both Samples F and N contain sodium chloride. The results are set forth below in Table 12.

TABLE 12

| | Sample C | | | Sample D | | | Sample F | | | Sample N | | |
|---|---|---|---|---|---|---|---|---|---|---|---|---|
| Microbe | 0.10% | 0.25% | 0.50% | 0.10% | 0.25% | 0.50% | 0.10% | 0.25% | 0.50% | 0.10% | 0.25% | 0.50% |
| *Candida albicans* | 4.18 | 4.35 | 4.56 | 3.65 | 3.75 | 4.51 | 4.35 | 4.81 | 4.56 | 4.35 | 4.88 | 6.35 |
| *Staphylococcus aureus* | 3.89 | 4.19 | 4.37 | 3.59 | 3.97 | 4.19 | 4.07 | 4.24 | 4.37 | 3.02 | 3.13 | 4.37 |
| *Staphylococcus epidermidis* | 3.39 | 3.50 | 3.65 | 3.39 | 3.47 | 3.75 | 3.95 | 4.35 | 4.39 | 3.87 | 3.50 | 4.75 |
| *Escherichia coli* | 3.01 | 3.29 | 3.52 | 2.87 | 3.17 | 3.29 | 2.87 | 2.65 | 3.65 | 4.13 | 3.99 | 4.29 |
| *Salmonella abony* | 3.04 | 3.34 | 3.39 | 2.70 | 2.86 | 3.04 | 2.86 | 3.34 | 3.39 | 3.56 | 3.86 | 4.44 |
| *Listeria monocytogenes* | 3.72 | 3.87 | 3.99 | 3.49 | 3.77 | 3.91 | 3.29 | 3.97 | 4.37 | 2.99 | 4.87 | 6.87 |
| Average, all microbes | 3.54 | 3.76 | 3.91 | 3.28 | 3.50 | 3.78 | 3.57 | 3.89 | 4.12 | 3.65 | 4.04 | 5.18 |
| Std. Dev. | 0.43 | 0.41 | 0.43 | 0.36 | 0.38 | 0.50 | 0.59 | 0.71 | 0.44 | 0.52 | 0.65 | 1.03 |

The superior performance of Samples F and N at thirty seconds, are notable when comparing the number of tests in which the Log Reduction was at least 4 (i.e. removal of >99.99% of the microbial population). Samples F and N exceeded this threshold 19 times, whereas the comparative benzalkonium chlorides (Samples C and D) only exceeded the Log 4 threshold seven times.

A further antimicrobial test was conducted to determine the log reduction at 10 minutes. Samples C, D, F, and N are as defined above. The results are set forth in Table 13.

TABLE 13

| | Sample C | | | Sample D | | | Sample F | | | Sample N | | |
|---|---|---|---|---|---|---|---|---|---|---|---|---|
| Microbe | 0.10% | 0.25% | 0.50% | 0.10% | 0.25% | 0.50% | 0.10% | 0.25% | 0.50% | 0.10% | 0.25% | 0.50% |
| *Candida albicans* | 5.95 | 6.35 | 6.43 | 4.84 | 5.55 | 5.77 | 6.25 | 6.25 | 6.43 | 5.65 | 5.63 | 6.77 |
| *Staphylococcus aureus* | 5.86 | 6.07 | 5.05 | 5.37 | 5.67 | 5.97 | 6.02 | 6.02 | 6.05 | 4.16 | 4.41 | 4.63 |
| *Staphylococcus epidermidis* | 4.79 | 5.05 | 5.05 | 4.47 | 4.98 | 5.05 | 5.05 | 5.25 | 5.35 | 5.05 | 4.05 | 5.05 |
| *Escherichia coli* | 4.59 | 5.07 | 5.07 | 4.62 | 4.77 | 5.07 | 5.07 | 5.07 | 5.07 | 4.75 | 5.21 | 4.87 |
| *Salmonella abony* | 4.44 | 4.50 | 4.50 | 4.14 | 4.34 | 4.55 | 3.50 | 4.50 | 4.50 | 4.04 | 4.56 | 4.70 |
| *Listeria monocytogenes* | 5.60 | 5.99 | 6.02 | 5.61 | 5.97 | 6.02 | 4.93 | 4.99 | 5.99 | 5.66 | 6.17 | 7.06 |
| Average, all microbes | 5.21 | 5.51 | 5.35 | 4.84 | 5.21 | 5.41 | 5.14 | 5.35 | 5.57 | 4.89 | 5.01 | 5.51 |
| Std. Dev. | 0.62 | 0.67 | 0.66 | 0.51 | 0.56 | 0.55 | 0.89 | 0.61 | 0.66 | 0.64 | 0.74 | 1.00 |

Samples F and N again showed an improved result in Log Reduction as compared to the comparative benzalkonium chlorides (Samples C and D).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method of disinfecting or sanitizing, wherein the method comprises:

contacting an aqueous composition comprising a component selected from the group consisting of chlorhexidine diglucoheptonate, benzalkonium glucoheptonate, and combinations thereof with a microbial population;

wherein, when the aqueous composition comprises chlorhexidine diglucoheptonate, the chlorhexidine diglucoheptonate comprises chlorhexidine di-α-glucoheptonate and chlorhexidine di-β-glucoheptonate and ratio of chlorhexidine di-β-glucoheptonate to chlorhexidine di-α-glucoheptonate is 1.5 or greater; and wherein, when the aqueous composition comprises benzalkonium glucoheptonate, the benzalkonium glucoheptonate comprises 90% or greater of benzalkonium α-glucoheptonate.

2. The method of claim 1, wherein a Log Reduction of the microbial population is 3 or greater, 30 seconds after application.

3. The method of claim 1, wherein the aqueous composition further comprises glucoheptonic acid.

4. The method of claim 3, wherein the aqueous composition comprises α-glucoheptonic acid and β-glucoheptonic acid and the composition comprises an α-glucoheptonic acid concentration, based on total isomers of glucoheptonic acid, of 90% or greater.

5. The method of claim 1, wherein the chlorhexidine diglucoheptonate comprises from 60% to 75% chlorhexidine di-β-glucoheptonate (chlorhexidine di-β73-glucoheptonate).

6. The method of claim 1, wherein the chlorhexidine diglucoheptonate comprises 81% chlorhexidine di-β-glucoheptonate (chlorhexidine di-β81-glucoheptonate).

7. The method of claim 1, wherein the aqueous composition comprises benzalkonium glucoheptonate.

8. The method of claim 1, wherein the microbial population comprises *C. albicans; S. aureus, S. epidermidis, E. coli, S. abony, L. monocytogenes*, or combinations thereof.

9. The method of claim 1, wherein the microbial population comprises SARS-COV-2.

10. The method of claim 7, wherein the benzalkonium glucoheptonate is prepared by a method comprising:

combining a benzalkonium salt and a glucoheptonate salt in a container and stirring the combination;

wherein the glucoheptonate salt comprises 90% or greater of an α-glucoheptonate salt.

11. The method of claim 1, wherein the benzalkonium glucoheptonate comprises 96% or greater of benzalkonium α-glucoheptonate.

12. The method of claim 1, wherein the benzalkonium glucoheptonate comprises 98% or greater of benzalkonium α-glucoheptonate.

13. The method of claim 1, wherein the benzalkonium glucoheptonate comprises 99% or greater of benzalkonium α-glucoheptonate.

14. The method of claim 1, wherein the chlorhexidine diglucoheptonate comprises from 61% to 73% chlorhexidine di-β-glucoheptonate.

15. The method of claim 1, wherein the chlorhexidine diglucoheptonate comprises from 61% to 71% chlorhexidine di-β-glucoheptonate.

16. The method of claim 1, wherein the chlorhexidine diglucoheptonate comprises from 65% to 71% chlorhexidine di-β-glucoheptonate.

17. The method of claim 1, wherein the chlorhexidine diglucoheptonate comprises from 67% to 71% chlorhexidine di-β-glucoheptonate.

18. The method of claim 1, wherein the chlorhexidine diglucoheptonate comprises from 68% to 71% chlorhexidine di-β-glucoheptonate.

19. A method of preparing chlorhexidine diglucoheptonate, the method comprising:

combining chlorhexidine and water to form a slurry; and adding glucoheptonic acid to the slurry and mixing the combination;

wherein the glucoheptonic acid comprises α-glucoheptonic acid and β-glucoheptonic acid and ratio of β-glucoheptonic acid and α-glucoheptonic acid is 1.5 or greater.

20. The method of claim 19, wherein the chlorhexidine diglucoheptonate has a molar ratio of glucoheptonic acid to chlorhexidine of from 1.5:1 to 3:1.

* * * * *